US009795652B2

(12) United States Patent
Pennypacker et al.

(10) Patent No.: US 9,795,652 B2
(45) Date of Patent: Oct. 24, 2017

(54) USE OF ENDOGENOUS ANTIOXIDANT PROTEINS IN THE TREATMENT OF STROKE

(75) Inventors: Keith Ronald Pennypacker, Wesley Chapel, FL (US); Alison Elizabeth Willing, Tampa, FL (US)

(73) Assignee: University of South Florida, Tampa, FL (US)

( * ) Notice: Subject to any disclaimer, the term of this patent is extended or adjusted under 35 U.S.C. 154(b) by 342 days.

(21) Appl. No.: 13/595,130

(22) Filed: Aug. 27, 2012

(65) Prior Publication Data

US 2013/0129673 A1    May 23, 2013

Related U.S. Application Data

(63) Continuation of application No. PCT/US2011/026284, filed on Feb. 25, 2011.

(60) Provisional application No. 61/308,017, filed on Feb. 25, 2010, provisional application No. 61/373,035, filed on Aug. 12, 2010.

(51) Int. Cl.
*A61K 38/20* (2006.01)
*G01N 33/68* (2006.01)
*A61K 38/19* (2006.01)

(52) U.S. Cl.
CPC ........ *A61K 38/2093* (2013.01); *A61K 38/193* (2013.01); *G01N 33/6896* (2013.01); *G01N 2800/2871* (2013.01)

(58) Field of Classification Search
None
See application file for complete search history.

(56) References Cited

U.S. PATENT DOCUMENTS

| | | | |
|---|---|---|---|
| 7,125,997 B2 | 10/2006 | Chyba et al. | |
| 2004/0197310 A1 | 10/2004 | Sanberg et al. | |
| 2005/0009096 A1 | 1/2005 | Genain et al. | |
| 2005/0169902 A1 | 8/2005 | Borlongan et al. | |
| 2005/0244965 A1* | 11/2005 | Weiss | 435/368 |
| 2005/0249708 A1 | 11/2005 | Garbuzova-Davis et al. | |
| 2006/0159666 A1* | 7/2006 | Willing | A61K 35/51 424/93.7 |
| 2006/0233765 A1 | 10/2006 | Messina et al. | |
| 2008/0175894 A1* | 7/2008 | Schaebitz et al. | 424/450 |

FOREIGN PATENT DOCUMENTS

WO    2007140971 A2    12/2007

OTHER PUBLICATIONS

Koh et al. Brain Res 1229: 233-248, 2008.*
Suzuki et al (J Cereb Blood Flow & Metab 25: 685-693, 2005).*
Route of Administration-from Wikipedia—May 6, 2015.*
Pan et al (Am J Physiol Cell Physiol 294: C1436-C1442, 2008).*
Pan et al (J Immunol 174, 119-125, 2006).*
Weiss et al (Biochimica et Biophysica Acta 1788: 842-857, 2009).*
Suzuki et al. (J Cereb Blood Flow Metab 20: 661-668, 2000).*
D.D. Rowe, C.C. Leonardo, A.A. Hall, M.D. Shahaduzzaman, L.A. Collier, A.E. Willing, K.R. Pennypacker, Cord blood administration induces oligodendrocyte survival through alterations in gene expression, Brain Research (2010), vol. 1366, pp. 172-188.
P. Gelosa, C. Banfi, M. Brioschi, E. Nobili, A. Gianella, U. Guerrini, A. Pignieri, E. Tremoli, L. Sironi, S 35171 exerts protective effects in spontaneously hypertensive stroke-prone rats by preserving mitochondrial function, European Journal of Pharmacology 604 (2009) pp. 117-124.
S. Suzuki, Y. Masui, M. Ohnuki, G. Miyakoda, T. Mori, K. Nakajima, M. Sato, Induction of Metallothionein Synthesis by Cilostazol in Mice and in Human Cultured neuronal Cell Lines, Biol. Pharm. Bull. (2007) 30(4) pp. 791-794.
V. Kumar, N. Kitaeff, M. Hampton, M. Cannell, C.C. Winterbourn, Reversible oxidation of mitochondrial peroziredoxin 3 in mouse heart subjected to ischemia and reperfusion, FEBS Letters 583 (2009) pp. 997-1000.
Menno van lookeren Campagne, Harold Thibodeaux, Nick van Bruggen, Belinda Cairns, Robert Gerlai, James T. Palmer, Simon P. Williams, David F. Lowe, Evidence for a protective role of metallothionein-1 in focal cerebral ischemia, PNAS (1999) vol. 96, No. 22, pp. 12870-12875.
Hall, A.A., et al., 2009. Human umbilical cord blood cells directly suppress ischemic oligodendrocyte cell death. J Neurosci Res. 87, 333-41.
Lloyd-Jones, D., et al., 2009. Heart disease and stroke statistics—2009 update: a report from the American Heart Association Statistics Committee and Stroke Statistics Subcommittee. Circulation. 119, 480-6.
Florencia Labombarda et al., Effects of Progesterone on Oligodendrocyte Progenitors, Oligodendrocyte Transcription Factors, and Myelin Proteins Following Spinal Cord Injury, GLIA, vol. 57, pp. 884-897 (Dec. 2, 2008).
Baumann, N. and Pham-Dinh, D., 2001. Biology of oligodendrocyte and myelin in the mammalian central nervous system. Physiol Rev. vol. 81 (2), pp. 871-927 (Apr. 2001).
Arai, K. and Lo, E.H., 2009. Experimental models for analysis of oligodendrocyte pathophysiology in stroke. Exp Transl Stroke Med. 1, 6.

(Continued)

*Primary Examiner* — Daniel E Kolker
*Assistant Examiner* — Aditi Dutt
(74) *Attorney, Agent, or Firm* — Robert J. Varkonyi; Smith & Hopen, P.A.

(57) ABSTRACT

Oligodendrocytes (OLs), the predominant cell type found in cerebral white matter, are essential for structural integrity and proper neural signaling. Very little is known concerning stroke-induced OL dysfunction. Infusion of human umbilical cord blood (HUCB) cells protects striatal white matter tracts in vivo and directly protects mature primary OL cultures from oxygen glucose deprivation (OGD). Microarray studies of RNA prepared from OL cultures subjected to OGD and treated with HUCB cells showed an increase in the expression of 33 genes associated with OL proliferation, survival, and repair functions, such as myelination. Immunohistochemistry showed antioxidant protein expression was upregluated in the ipsilateral white matter tracts of rats infused with HUCB cells 48 hrs after middle cerebral artery occlusion (MCAO). These results show expression of genes induced by HUCB cell therapy that could confer oligoprotection from ischemia.

8 Claims, 36 Drawing Sheets

(56) References Cited

OTHER PUBLICATIONS

International Search Report for PCT/US2011/026284 dated Dec. 27, 2011.
Kaplan, M.R., et al., 1997. Induction of sodium channel clustering by oligodendrocytes. Nature. 386, 724-8.
Sheng, W., et al., 2005. The roles of versican V1 and V2 isoforms in cell proliferation and apoptosis. Mol Biol Cell. 16, 1330-40.
Wilkins, A., et al., 2003. Oligodendrocytes promote neuronal survival and axonal length by distinct intracellular mechanisms: a novel role for oligodendrocyte-derived glial cell line-derived neurotrophic factor. J Neurosci. 23, 4967-74.
Lyons, S.A. and Kettenmann, H., 1998. Oligodendrocytes and microglia are selectively vulnerable to combined hypoxia and hypoglycemia injury in vitro. J Cereb Blood Flow Metab. 18, 521-30.
Sanberg, P.R., et al., 2005. Umbilical cord blood-derived stem cells and brain repair. Ann N Y Acad Sci. 1049, 67-83.
Wang, M. et al., 2009. The immunomodulatory activity of human umbilical cord blood-derived mesenchymal stem cells in vitro. Immunology. 126, 220-32.
Newcomb, J.D., et al., 2006. Timing of cord blood treatment after experimental stroke determines therapeutic efficacy. Cell Transplant. 15, 213-23.
Newman, M.B., et al., 2005. Stroke-induced migration of human umbilical cord blood cells: time course and cytokines. Stem Cells Dev. 14, 576-86.
Vendrame, M., et al., 2004. Infusion of human umbilical cord blood cells in a rat model of stroke dose-dependently rescues behavioral deficits and reduces infarct volume. Stroke. 35, 2390-5.
Chua S.J., et al., 2010. The effect of umbilical cord blood cells on outcomes after experimental traumatic spinal cord injury. Spine (Phila Pa 1976). 35, 1520-6.
Neuhoff, S., et al., 2007. Proliferation, differentiation, and cytokine secretion of human umbilical cord blood-derived mononuclear cells in vitro. Exp Hematol. 35, 1119-31.
Gottschall, P.E., et al., 1995. Increased production of gelatinase B (matrix metalloproteinase-9) and interleukin-6 by activated rat microglia in culture. J Neurosci Res. 42, 335-42.
McCarthy, K.D. and de Vellis, J., 1980. Preparation of separate astroglial and oligodendroglial cell cultures from rat cerebral tissue. J Cell Biol. 85, 890-902.
Barres, B.A., et al., 1993. Multiple extracellular signals are required for long-term oligodendrocyte survival. Development. 118, 283-95.
Yang, Z., et al., 2005. Optimization of oligodendrocyte progenitor cell culture method for enhanced survival. J Neurosci Methods. 149, 50-6.
Jin, M.H., et al., 2005. Characterization of neural cell types expressing peroxiredoxins in mouse brain. Neurosci Lett. 381, 252-7.
Kursula, P., 2008. Structural properties of proteins specific to the myelin sheath. Amino Acids. 34, 175-85.
Miyazaki, I., et al., 2002. Age-related changes in expression of metallothionein-III in rat brain. Neurosci Res. 43, 323-33.
Sim, F.J., et al., 2008. Statin treatment of adult human glial progenitors induces PPAR gamma-mediated oligodendrocytic differentiation. Glia. 56, 954-62.
Butler, T.L., et al., 2002. Neurodegeneration in the rat hippocampus and striatum after middle cerebral artery occlusion. Brain Res. 929, 252-60.
Schachner, M., et al., 1981. Developmental expression in central and peripheral nervous system of oligodendrocyte cell surface antigens (O antigens) recognized by monoclonal antibodies. Dev Biol. 83, 328-38.
Sommer, I. and Schachner, M., 1982. Cell that are O4 antigen-positive and O1 antigen-negative differentiate into O1 antigen-positive oligodendrocytes. Neurosci Lett. 29, 183-8.
Dewar, D., et al., 2003. Oligodendrocytes and ischemic brain injury. J Cereb Blood Flow Metab. 23, 263-74.
Hofmann, B., et al., 2002. Peroxiredoxins. Biol Chem. 383, 347-64.
Valentin, F., et al., 2004. The mechanism of oxidative stress stabilization of the thromboxane receptor in COS-7 cells. J Biol Chem. 279, 8316-24.
Giguere, P., et al., 2007. Peroxiredoxin-4 interacts with and regulates the thromboxane A(2) receptor. FEBS Lett. 581, 3863-8.
Jang, H.H., et al., 2004. Two enzymes in one; two yeast peroxiredoxins display oxidative stressdependent switching from a peroxidase to a molecular chaperone function. Cell. 117, 625-35.
Kang, S.W., et al., 2005. 2-Cys peroxiredoxin function in intracellular signal transduction: therapeutic implications. Trends Mol Med. 11, 571-8.
Hozumi, I., et al., 1998. Brain injury and growth inhibitory factor (GIF)—a minireview. Neurochem Res. 23, 319-28.
Hwang, Y.P., et al., 2008. Metallothionein-III protects against 6-hydroxydopamine-induced oxidative stress by increasing expression of heme oxygenase-1 in a PI3K and ERK/Nrf2-dependent manner. Toxicol Appl Pharmacol. 231, 318-27.
Uchida, Y., et al., 2002. Growth inhibitory factor prevents neurite extension and the death of cortical neurons caused by high oxygen exposure through hydroxyl radical scavenging. J Biol Chem. 277, 32353-9.
Braughler, J.M., et al., 1986. The involvement of iron in lipid peroxidation. Importance of ferric to ferrous ratios in initiation. J Biol Chem. 261, 10282-9.
Connor, J.R. and Menzies, S.L., 1996. Relationship of iron to oligodendrocytes and myelination. Glia. 17, 83-93.
Juurlink, B.H., 1997. Response of glial cells to ischemia: roles of reactive oxygen species and glutathione. Neurosci Biobehav Rev. 21, 151-66.
Juurlink, et al., 1998. Peroxide-scavenging deficit underlies oligodendrocyte susceptibility to oxidative stress. Glia. 22, 371-8.
Dasari, V.R., et al., 2008. Neuroprotection by cord blood stem cells against glutamate-induced apoptosis is mediated by Akt pathway. Neurobiol Dis. 32, 486-98.
Morales-Ruiz, M., et al., 2000. Vascular endothelial growth factor-stimulated actin reorganization and migration of endothelial cells is regulated via the serine/threonine kinase Akt. Circ Res. 86, 892-6.
Six, I., et al., 2002. Akt signaling mediates VEGF/VPF vascular permeability in vivo. FEBS Lett. 532, 67-9.
Wegiel, B., et al., 2008. Interleukin-6 activates PI3K/Akt pathway and regulates cyclin A1 to promote prostate cancer cell survival. Int J Cancer. 122, 1521-9.
Liu, Y., et al., 2006. Evi1 is a survival factor which conveys resistance to both TGFbeta- and taxol-mediated cell death via PI3K/AKT. Oncogene. 25, 3565-75.
Moeenrezakhanlou, A., et al., 2008. Myeloid cell differentiation in response to calcitriol for expression CD11b and CD14 is regulated by myeloid zinc finger-1 protein downstream of phosphatidylinositol 3-kinase. J Leukoc Biol. 84, 519-28.
Yu, Y.L., et al., 2005. MAPK-mediated phosphorylation of GATA-1 promotes Bcl-XL expression and cell survival. J Biol Chem. 280, 29533-42.
Chiellini, C., et al., 2008. Stathmin-like 2, a developmentallyassociated neuronal marker, is expressed and modulated during osteogenesis of human mesenchymal stem cells. Biochem Biophys Res Commun. 374, 64-8.
Johns, T.G. and Bernard, C.C., 1999. The structure and function of myelin oligodendrocyte glycoprotein. J Neurochem. 72, 1-9.
Riederer, B.M., et al., 1997. Regulation of microtubule dynamics by the neuronal growth-associated protein SCG10. Proc Natl Acad Sci U S A. 94, 741-5.
Wood, P.M. and Bunge, R.P., 1991. The origin of remyelinating cells in the adult central nervous system: the role of the mature oligodendrocyte. Glia. 4, 225-32.
Belmont, L.D. and Mitchison, T.J., 1996. Identification of a protein that interacts with tubulin dimers and increases the catastrophe rate of microtubules. Cell. 84, 623-31.
Nakamura, S., et al., 2008. KIS induces proliferation and the cell cycle progression through the phosphorylation of p27Kip1 in leukemia cells. Leuk Res. 32, 1358-65.
Simons, M. and Trajkovic, K., 2006. Neuron-glia communication in the control of oligodendrocyte function and myelin biogenesis. J Cell Sci. 119, 4381-9.

(56) References Cited

OTHER PUBLICATIONS

Gong, Y., et al., 2006. Sterolregulated ubiquitination and degradation of Insig-1 creates a convergent mechanism for feedback control of cholesterol synthesis and uptake. Cell Metab. 3, 15-24.

Nguyen, A.D., et al., 2007. Hypoxia stimulates degradation of 3-hydroxy-3-methylglutaryl-coenzyme A reductase through accumulation of lanosterol and hypoxia-inducible factor-mediated induction of insigs. J Biol Chem. 282, 27436-46.

Birling, M.C., et al., 1999. A novel rat tetraspan protein in cells of the oligodendrocyte lineage. J Neurochem. 73, 2600-8.

Albers, Gregory W. et al. Antithrombotic and Thrombolytic Therapy for Ischemic Stroke. The Seventh ACCP Conference on Antithrombotic and Thrombolytic Therapy. Chest Journal, Sep. 2004 Supplement. vol. 126, pp. 483S-512S.

Jobes, David R. et al. Complications and Failures of Subclavian-Vein Catheterization. The New England Journal of Medicine, Jun. 8, 1995. 332(23), pp. 1579-1581.

Botha, et al., Postinjury neutrophil priming and activation: an early vulnerable window. Surgery. Aug. 1995;118 (2):358-64.

Hietbrink, et al., Trauma: the role of the innate immune system. World J Emerg Surg. May 20, 2006;1:15.

Iadecola & Anrather, The immunology of stroke: from mechanisms to translation. Nat Med. 2011;17(7):796-808.

Ikonomidou & Turski, Why did NMDA receptor antagonists fail clinical trials for stroke and traumatic brain injury Lancet Neural. Oct. 2002;1(6):383-6.

Lo, et al., Mechanisms, challenges and opportunities in stroke. Nat Rev Neurosci. May 2003;4(5):399-141.

Vidale, et al., Postischemic inflammation in acute stroke. J Clin Neurol. Jan. 2017;13(1):1-9.

Iadecola & Anrather, The immunology of stroke: from mechanisms to translation. Nat Med. Jul. 7, 2011;17(7):796-808.

Offner, et al., Experimental stroke induces massive, rapid activation of the peripheral immune system. J Cereb Blood Flow Metab. May 2006;26(5):654-65.

* cited by examiner

USE OF ENDOGENOUS ANTIOXIDANT PROTEINS IN THE TREATMENT OF STROKE

CROSS REFERENCE TO RELATED APPLICATION

This application is a continuation of and claims priority to International Patent Application No. PCT/US11/26284, entitled "Use of Endogenous Antioxidant Proteins in the Treatment of Stroke," filed Feb. 25, 2011 which is a non-provisional of and claims priority to U.S. Provisional Application 61/308,017, entitled "Use of Endogenous Antioxidant Proteins in the Treatment of Stroke", filed Feb. 25, 2010; and U.S. Provisional Application 61/373,035, entitled "Use of Leukemia Inhibitory Factor in the Treatment of Stroke", filed Aug. 12, 2010; which are fully incorporated herein by reference.

GOVERNMENT SUPPORT

This invention was made with government support under, grant no. NS039141 awarded by the National Institutes of Health. The government has certain rights in the invention.

FIELD OF INVENTION

This invention relates to treatment of CNS damage. Specifically, the invention provides for upregulating antioxidant proteins in neurons to effect treatment, and prevent neuronal damage.

BACKGROUND OF THE INVENTION

Stroke is the third leading cause of death in the United States, with ischemic strokes accounting for 83% of all strokes (Lloyd-Jones, D., et al., 2009. Heart disease and stroke statistics—2009 update: a report from the American Heart Association Statistics Committee and Stroke Statistics Subcommittee. Circulation. 119, 480-6). Ischemic brain injury affects both white and gray matter. Although white matter integrity is essential to proper neuronal communication, much of current research is focused exclusively on neuronal damage. Accounting for 50% of brain volume in humans, white matter and the oligodendroglia that myelinate these areas play an integral role in proper brain function (Miller, A. K., et al., 1980. Variation with age in the volumes of grey and white matter in the cerebral hemispheres of man: measurements with an image analyser. Neuropathol Appl Neurobiol. 6, 119-32). The myelin produced by OLs not only supports axonal structural integrity, but is also essential in impulse integration (Baumann, N. and Pham-Dinh, D., 2001. Biology of oligodendrocyte and myelin in the mammalian central nervous system. Physiol Rev. 81, 871-927). Thus, white matter protection is necessary to dampen stroke-induced injury and its progressive pathology (Arai, K. and Lo, E. H., 2009. Experimental models for analysis of oligodendrocyte pathophysiology in stroke. Exp Transl Stroke Med. 1, 6).

In addition to myelination, OLs support the survival and function of neurons by regulating axonal size and ion channel clustering. OLs also secrete trophic factors such as BDNF, NGF, GDNF and IGF-1, all of which aid in cell survival and maintenance (Baron-Van Evercooren, A., et al., 1991. Expression of IGF-I and insulin receptor genes in the rat central nervous system: a developmental, regional, and cellular analysis. J Neurosci Res. 28, 244-53; Kaplan, M. R., et al., 1997. Induction of sodium channel clustering by oligodendrocytes. Nature. 386, 724-8; Noble, M., et al., 2005 The Oligodendrocyte. Developmental Neurobiology, Vol., Plenum Publisher, New York; Wilkins, A., et al., 2003. Oligodendrocytes promote neuronal survival and axonal length by distinct intracellular mechanisms: a novel role for oligodendrocyte-derived glial cell line-derived neurotrophic factor. J. Neurosci. 23, 4967-74). Of the different types of glia, OLs are the most vulnerable to hypoxic and hypoglycemic conditions, yet the precise mechanisms underlying this susceptibility are unknown (Lyons, S. A. and Kettenmann, H., 1998. Oligodendrocytes and microglia are selectively vulnerable to combined hypoxia and hypoglycemia injury in vitro. J Cereb Blood Flow Metab. 18, 521-30).

HUCB cell therapy is an emerging treatment for CNS injury. The immaturity of HUCB cells contribute to the characteristic low immunogenicity (Sanberg, P. R., et al., 2005. Umbilical cord blood-derived stem cells and brain repair. Ann N Y Acad. Sci. 1049, 67-83). HUCB cells are less immunogenic than other stem cell treatments such as bone marrow and thus elicits lower immunomodulatory effects (Sanberg, P. R., et al., 2005. Umbilical cord blood-derived stem cells and brain repair. Ann N Y Acad. Sci. 1049, 67-83; Wang, M., et al., 2009. The immunomodulatory activity of human umbilical cord blood-derived mesenchymal stem cells in vitro. Immunology. 126, 220-32). In vivo, HUCB cells migrate to the site of injury, resulting in reduced infarct volumes, neuroprotection and preservation of white matter following MCAO (Hall, A. A., et al., 2009. Human umbilical cord blood cells directly suppress ischemic oligodendrocyte cell death. J Neurosci Res. 87, 333-41; Newcomb, J. D., et al., 2006. Timing of cord blood treatment after experimental stroke determines therapeutic efficacy. Cell Transplant. 15, 213-23; Newman, M. B., et al., 2005. Stroke-induced migration of human umbilical cord blood cells: time course and cytokines Stem Cells Dev. 14, 576-86; Vendrame, M., et al., 2004. Infusion of human umbilical cord blood cells in a rat model of stroke dose-dependently rescues behavioral deficits and reduces infarct volume. Stroke. 35, 2390-5). Furthermore, multipotential stem cells derived from HUCB cells secrete neuroprotective, angiogenic and anti-inflammatory factors resulting in a functional recovery in spinal cord injuries (Chua, S. J., et al., 2010. The effect of umbilical cord blood cells on outcomes after experimental traumatic spinal cord injury. Spine (Phila Pa. 1976). 35, 1520-6). In vitro experiments showed that in addition to growth factors, HUCB cells secrete cytokines, matrix metalloproteinase inhibitors, and interleukins (Neuhoff, S., et al., 2007. Proliferation, differentiation, and cytokine secretion of human umbilical cord blood-derived mononuclear cells in vitro. Exp Hematol. 35, 1119-31). Additionally, HUCB cells co-incubated with OLs reduced OGD-induced apoptosis by decreasing activated caspase 3 (Hall, A. A., et al., 2009. Human umbilical cord blood cells directly suppress ischemic oligodendrocyte cell death. J Neurosci Res. 87, 333-41). Despite these potent protective actions and known soluble factors, the precise pathways involved in HUCB cell-mediated OL survival have yet to be elucidated.

Therefore, what is needed is a method of targeting olidodendrocyte protection and repair during and after stroke and central nervous system infarct.

SUMMARY OF THE INVENTION

Changes in the gene expression profiles of primary OL cultures subjected to OGD were examined to elucidate the protective pathways induced by co-incubation with HUCB cells. Microarray results revealed that 33 genes were significantly increased in OLs co-incubated with HUCB cells and exposed to OGD. Thus, stroke-induced oligodendrocytes death may be treated by administering an ischemia-reducing factor, wherein the ischemia-reducing factor is leukemia inhibitory factor, granulocyte colony stimulating factor, or a combination thereof. The ischemia-reducing factor increases expression of anti-oxidant protein in the external capsule following MCAO. The ischemia-reducing factors may be secreted by human umbilical cord blood cells. In particular variations of the invention, the human umbilical cord blood cells are administered at $3.33 \times 10^6$ to $2.86 \times 10^6$ cells per kg. The ischemia-reducing factor causes upregulation of the following genes, confirmed by qRT-PCR: Uhmk1, Insig1, Mt3, Tspan2, Prdx4, Stmn2, MOG, and Vcan gene expression. Immunohistochemical analysis of tissues from rats treated with HUCB cells 48 hrs after MCAO demonstrated increased protein expression of Uhmk1, Insig1, Mt3, Tspan2, Prdx4, and MOG.

The ischemia-reducing factors are preferably administered within 48 hours of the stroke. In addition, the ischemia-reducing factors may be administered in normoxic cells, thereby aiding in the survival and repair of cells outside of the range of the infarct.

Administering ischemia-reducing factors may also be used to enhance replacement of membrane lipids that are degraded in response to neuronal injury, causing increased expression of anti-oxidant protein in the external capsule following MCAO. The ischemia-reducing factors are preferably administered within 48 hours of the stroke, but may also be administered to normoxic cells to aid in the survival and repair of cells outside of the range of the infarct. In variations of the invention, the ischemia-reducing factors are secreted by human umbilical cord blood cells, for which the human umbilical cord blood cells may be administered at $3.33 \times 10^6$ to $2.86 \times 10^6$ cells per kg. The ischemia-reducing factors may induce cholesterol biosynthesis, wherein the cholesterol biosynthesis restores the cell membrane or remyelinates neuronal cells.

Administering ischemia-reducing factors may also be used to upregulate the production of anti-oxidant proteins in oligodendrocytes, where the anti-oxidant is Uhmk1, MOG, Insig1, Mt3, Prdx4, Stmn2, or combinations thereof. In particular variations of the invention, the anti-oxidant is Prdx4, Mt3, or combinations thereof. Preferably, the ischemia-reducing factors are administered within 48 hours of the stroke, such as by administration of human umbilical cord blood cells, which then secrete the ischemia-reducing factors. The human umbilical cord blood cells may be administered at $3.33 \times 10^6$ to $2.86 \times 10^6$ cells per kg.

The vitality status of oligodendrocytes may also be determined by collecting a test sample of oligodendrocytes and testing the test sample of oligodendrocytes for expression of at least one gene product, wherein the gene product is MOG, Insig1, Prdx4, Mt3, or Vcan. The results from the test sample of oligodendrocyte are then compared to a sample of normal oligodendrocytes or result data obtained from normal oligodendrocytes, allowing a determination to be made based on a drop in expression of the at least one gene product when compared to normal oligodendrocytes, indicating oligodendrocyte death. In particular, the analysis is especially useful to determine ischemic oligodendrocyte cell death.

The testing for expression of the at least one of gene product may be via immunohistochemistry, microarray, or PCR. For example, where the gene products may be tested to identify the staining patterns of gene products using immunohistochemistry. Staining patterns, such as staining in the extracellular space for MOG, Vcan, or a combination thereof; or cell bodies staining for Insig1, Prdx4, Mt3, or a combination thereof, may be used to determine oligodendrocyte vitality status. In double staining immunohistochemistry, the test sample is double labeled for a first gene product and a second gene product. The first gene product may be Uhmk1, MOG, Insig1, Mt3, Tspan2, Prdx4, Stmn2, or Vcan; while the second gene product is RIP, CD11b, or GFAP.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
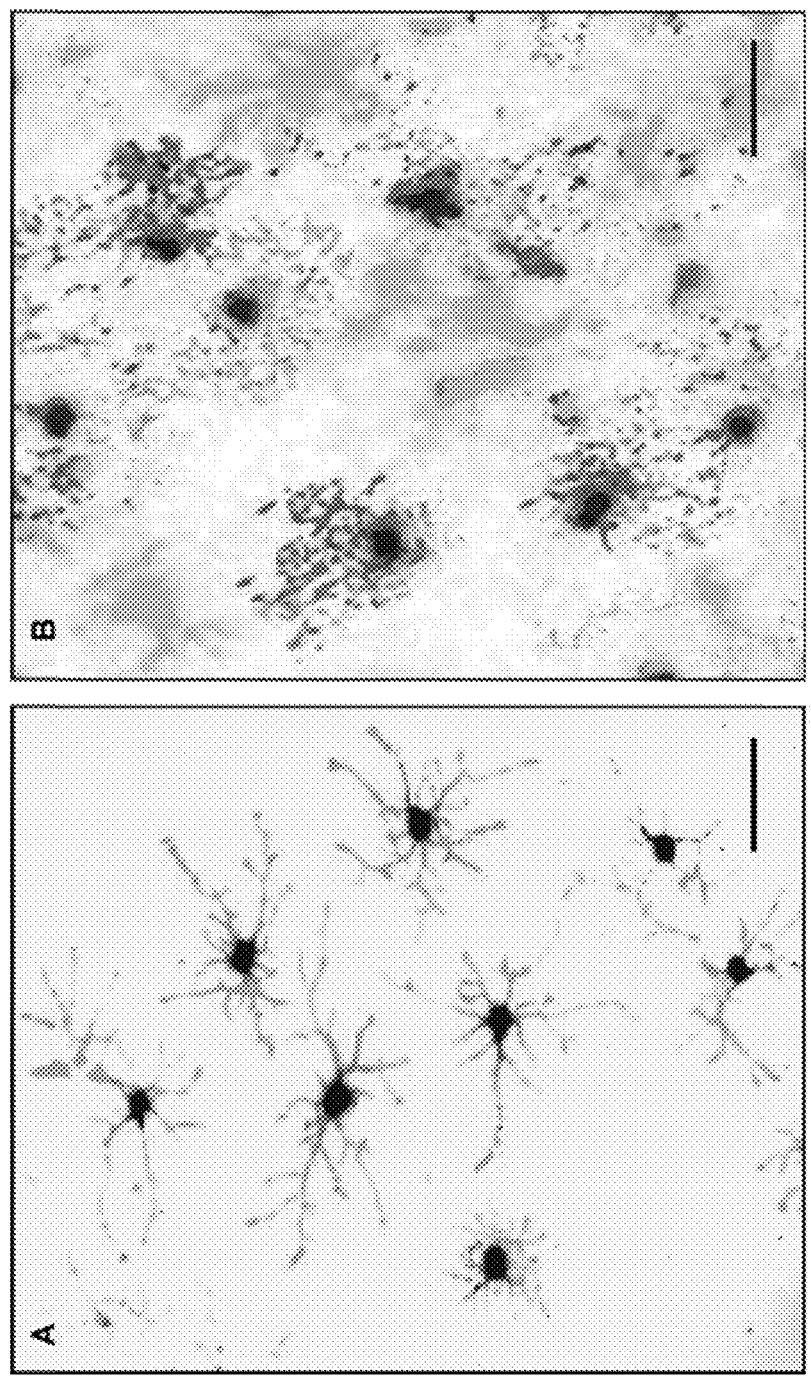
FIGS. 1(A) and (B) are images showing OLs differentiate into the mature phenotype. Photomicrographs show immunofluorescent staining of OL cultures at selected time points following PDGF-AA withdrawal. (A) 6 hrs after withdrawal, NG2 (light gray) and O4 (dark gray) colocalized in OLs that exhibited both bipolar and immature morphology, as indicated by the lateralized orientation of processes and the relatively low number of processes, respectively. (B) At 36 hrs, NG2-positive OLs light gray) expressed MBP (dark gray) and contained greater numbers of processes, indicating that this withdrawal period was sufficient for differentiation into the mature phenotype. Scale bars=50 μm.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

OL, oligodendrocyte; HUCB, human umbilical cord blood; OGD, oxygen glucose deprivation; Uhmk1, U2AF homology motif kinase 1; Insig1, insulin induced gene 1; Mt3, metallothionein 2; Tspan2, tetraspanin 2; Prdx4, peroxiredoxin 4; Stmn2, stathmin-like 2; MOG, myelin oligodendrocyte glycoprotein; Vcan, versican; MCAO, middle cerebral artery occlusion; BDNF, brain derived neurotrophic factor; NGF, nerve growth factor; GDNF, glial cell derived neurotrophic factor; IGF-1, insulin like growth factor 1; DMEM, Dulbecco modified eagle medium; PDGF-AA, platelet derived growth factor-AA; LDH, lactate dehydrogenase; GADPH, glyceraldehyde-3-phosphate dehydrogenase; NG2, chondroitin sulfate proteoglycan; O4, Oligodendrocyte marker O4; MBP, myelin basic protein; GFAP, glial fibrillary acidic protein; RIP, Receptor interacting protein; EVI1, ecotropic viral integration site 1; MZF1, myeloid zinc finger protein; GATA1, GATA-binding factor 1; NK6.1, NK6 homeobox 1; PAX6, pax-6 paired domain binding site; Sox-5, SRY (sex determining region Y)-box 5; SRF, serum response factor; ROS, reactive oxygen species; VEGF, vascular endothelial growth factor; IL-6, interleukin 6; H-I, hypoxic ischemia; AU, absorbance units.

Human umbilical cord blood (HUCB) cells were collected via methods described in the art by Borlongan, et al. (U.S. application Ser. No. 11/012,849), Garbuzova-Davis, et al. (U.S. application Ser. No. 10/908,322), and Sanberg, et al. (U.S. application Ser. No. 10/777,425). A mixture of monocytes lymphocytes and small population of stem cells were administered intravenously 48 hrs following stroke. Analysis of the cell composition showed 22.9±7.2% were monocytes, 77.05±7.24% were lymphocytes, 46.59±15.62% were T lymphocytes, and 0.54±0.24% were $CD34^+$.

All animal procedures were conducted in accordance with the NIH Guide for the Care and Use of Laboratory Animals with a protocol approved by the Institutional Animal Care and Use Committee at the University of South Florida. Experiments were designed to minimize the number of animals required. Sprague-Dawley rats were purchased from Harlan Labs (Indianapolis, Ind.), maintained on a 12 hr light/dark cycle (7 am-7 pm) in a climate-controlled room, and allowed access to food and water ad libitum. Neonatal rats birthed from untimed-pregnant dams were used for in vitro experiments and 300-350 g male rats were used for in vivo experiments. Measures taken to minimize pain and discomfort are described in the subsequent methodology.

Determination of promoter response elements were determined using accession numbers of OL genes shown by microarray and confirmed by qRT-PCR to increase expression were entered into Genomatix software (ElDorado/Gene2Promoter v4.7.0; Genomatix Software Inc, Ann Arbor, Mich.). The promoter regions of selected genes were investigated for common transcription factor binding sites. Transcription factor families were determined and transcription factor binding sites conserved across the promoter regions of all selected genes were identified.

All RNA collection and purification steps were performed under nuclease-free conditions using DNAse/RNAse-free materials. For RNA lysate collection, 10 μl of β-mercaptoethanol (Pharmacia Biotech, Uppsala, Sweden) was added to 1 ml RTL buffer (Qiagen Inc., Valencia, Calif.) and 350 μl of the resulting mixture was added to each OL-containing well to lyse the cells. Cell lysates were then collected and stored at −80° C. prior to extracting the RNA. Qiagen's RNeasy Mini Kit was used to extract total RNA from each cell lysate using the optional Qiagen RNase-Free DNase set for DNase digestion (Qiagen Inc). Following the extraction, 1 μl of each RNA sample was tested in an Agilent 2100 Bio-analyzer to determine the purity and quantity of RNA present. The remaining sample was stored at −80° C. for subsequent use with gene array.

Data from all experiments were quantified and analyzed using GraphPad Prism 4.0 (GraphPad Software, La Jola, Calif.) software. Main effects were determined using one-way ANOVAs, followed by Dunnett's post hoc tests to detect significant differences across treatment groups. When two variables were present, two-way ANOVAs were used followed by Bonferroni post hoc tests. A "p" value<0.05 was used as the threshold for significant differences.

Example 1

Mixed glial cultures were prepared using postnatal day 3 rat pups. The pups were decapitated, brains removed, and meninges dissected away. Rat cortices were dissociated in a solution of 0.25% trypsin/2.21 mM EDTA, triturated, and pelleted. The pellet was re-suspended in DMEM (Mediatech, Manassas, Va.) supplemented with 2.5% fetal bovine serum, 10% horse serum, and 1% antibiotic/antimycotic (DMEM$^+$). Trypan Blue exclusion was used to assess cell viability. Cells were seeded ($1.5 \times 10^7$) into poly-lysine-treated 75 cm$^2$ tissue culture flasks. Media was changed with fresh DMEM$^+$ the following day and cultures were incubated for 8 days at 37° C. (Gottschall, P. E., et al., 1995. Increased production of gelatinase B (matrix metalloproteinase-9) and interleukin-6 by activated rat microglia in culture. J Neurosci Res. 42, 335-42).

Oligodendrocytes were purified from the mixed glial cultures by mechanically shaking the cultures for 1 hr to separate microglial cells from the OL/astrocyte monolayer and media was discarded. Fresh DMEM$^+$ was added and the flask was returned to the incubator for an additional 2 days at 37° C. The mixed glial preparations were then shaken for 18 hrs to separate OLs and microglia from the astrocyte monolayer. The media was removed, the cells were pelleted and resuspended in DMEM$^+$. Viable cells were then counted using Trypan Blue exclusion. Microglia- and OL-containing media was added to 10 cm plastic tissue culture dishes at a density of $1 \times 10^7$ cells/dish and incubated for 15 min at 37° C. (procedure repeated 3 times for microglial adherence to the plastic). After incubation, the dishes were gently swirled and media collected. The remaining suspension was pelleted, re-suspended in DMEM$^+$, and plated on glass poly-lysine-treated coverslips at $3 \times 10^5$ cells/coverslip (McCarthy, K. D. and de Vellis, J., 1980. Preparation of separate astroglial and oligodendroglial cell cultures from rat cerebral tissue. J. Cell Biol. 85, 890-902). The following day, media was changed to Neurobasal complete (Neurobasal supplemented with B-27, L-glutamine 0.5 mM, and 10 ng/ml PDGF AA) (Barres, B. A., et al., 1993. Multiple extracellular signals are required for long-term oligodendrocyte survival. Development. 118, 283-95; Yang, Z., et al., 2005. Optimization of oligodendrocyte progenitor cell culture method for enhanced survival. J Neurosci Methods. 149, 50-6). OLs remained in Neurobasal complete and PDGFAA for 7 days to encourage proliferation. After the proliferation period, PDGF-AA was withdrawn for 5 days to induce OL differentiation into the mature phenotype (Yang, Z., et al., 2005. Optimization of oligodendrocyte progenitor cell culture method for enhanced survival. J Neurosci Methods. 149, 50-6). Experiments were conducted immediately following the 5 day PDGF-AA withdrawal. All in vitro experiments were conducted using >95% pure OL cultures, as previously described in (Hall, A. A., et al., 2009. Human umbilical cord blood cells directly suppress ischemic oligodendrocyte cell death. J Neurosci Res. 87, 333-41).

OLs were characterized using antibodies specific for NG2, O4 and MBP in double immunofluorescence staining to determine OL developmental stage in vitro, as seen in FIGS. 1(A) to (B). NG2 is a reliable marker throughout the course of OL differentiation in vitro, while O4 is expressed by immature OLs. Furthermore, the expression of myelinating proteins such as MBP denotes the mature OL phenotype. Six hours following PDGF-AA withdrawal, NG2 and O4 colocalized in OLs with immature morphology as indicated by the relatively low number of processes, seen in FIG. 1(A). MBP was not detected at this time point. By 36 hrs following PDGF-AA removal, colocalization of NG2 and MBP, seen in FIG. 1(B), was evident in OL cultures. The prominent upregulation of MBP and the increased number of OL processes at 36 hrs signifies the progression of OLs to the mature phenotype that is present in the adult rat brain.

To analyze the oligodendrocytes in ischemic conditions, OLs were subjected to oxygen glucose deprivation (OGD). OLs were seeded onto glass coverslips and randomly assigned to one of two conditions: OGD (DMEM without glucose) or normoxia (DMEM with glucose). Transwell inserts (0.2 μm: Nalge Nunc International, Rochester, N.Y.) were added to 6-well plates containing coverslips. The inserts provided a barrier that prevented OL-HUCB cell contact but was permeable to media and soluble factors. Cryopreserved HUCB cells (ALLCELLS, Emeryville, Calif.) were rapidly thawed, washed, pelleted to remove the cryopreservatives and re-suspended in 10 ml DMEM with glucose and DNase (Sigma-Aldrich, St. Louis, Mo.; 50 kunitz units/ml). HUCB cells were seeded onto tissue culture inserts ($1 \times 10^5$ cells/insert) and placed into the wells containing OL coverslips immediately prior to OGD exposure. Experimental groups not subjected to HUCB cell treatment received inserts containing an equal volume of DNase-supplemented DMEM with glucose. A negative control of media alone and wells containing $1 \times 10^5$ HUCB cells with DNase were included as controls to quantify HUCB cell contribution to the LDH assay for each experimental condition.

Cells undergoing OGD were placed in an air-tight hypoxia chamber. The chamber was then flushed with hypoxic gas (95% $N_2$, 4% $CO_2$, 1% $O_2$; Airgas, Tampa, Fla.) for 15 min and sealed for the duration of exposure. Normoxic cells were maintained in a standard tissue culture incubator. Cultures were subjected to OGD or normoxia for 24 hrs at 37° C. The media from each well was collected, clarified by centrifugation, and LDH analysis was performed immediately.

OL cell death in culture was determined using the LDH assay (Takara Bio, Inc., Madison, Wis.), since cell death is associated with LDH release through the plasma membrane. LDH is present in a large number of tissues, like the heart, liver, kidney, skeletal muscle, brain, blood cells, and lungs. Tissue breakdown releases LDH, thereby elevating circulating LDH and indicating tissue damage. Briefly, 100 µl of tissue culture media from each experimental group was added to a 96-well plate and 100 µl of LDH reagent was added to each well. Plates were incubated for 30 min at 25° C. and absorbances were read on a microplate reader at a 548 nm wavelength. The media from HUCB cell only cultures served as a control for HUCB cell death. The absorbance of HUCB cell only media, as well as the absorbance of media only, was subtracted from the total absorbance of the OL wells to eliminate background LDH activity.

Figure 2:
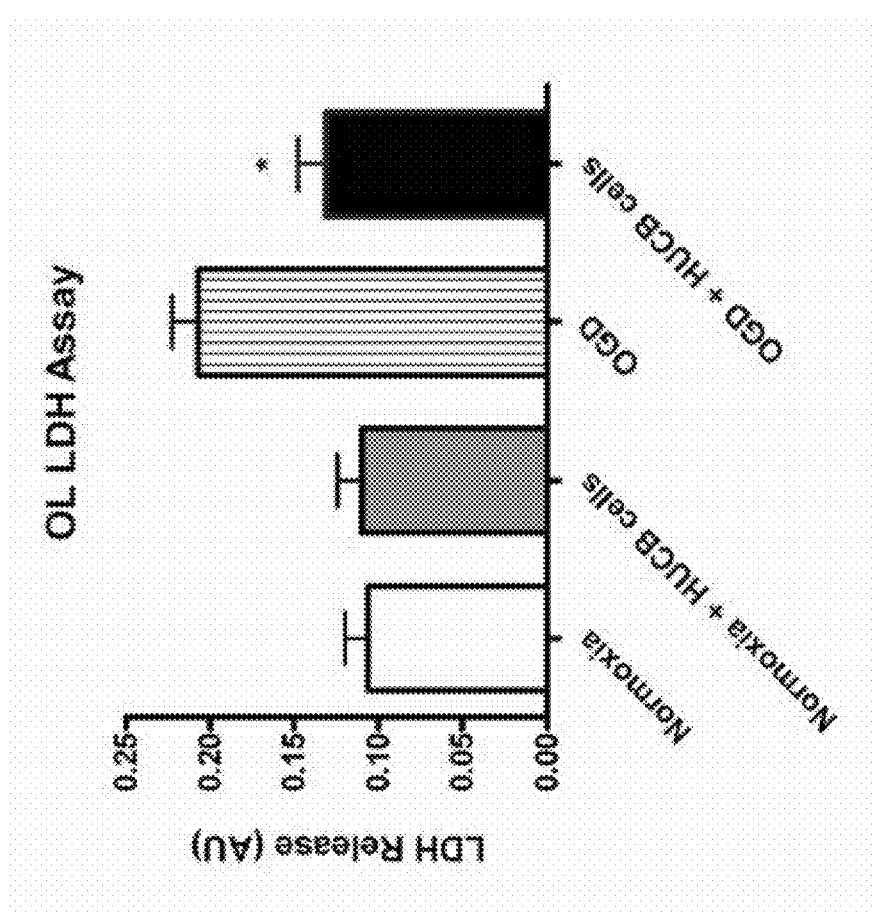
FIG. 2 is a graph showing HUCB cells decrease LDH release from OLs subjected to 24 hrs OGD. Media from OL cultures subjected to OGD-only contained elevated levels of LDH compared to media from normoxic controls, demonstrating OGD-induced cellular injury. OL cultures subjected to OGD were rescued by co-incubation with HUCB cells, as LDH release was reduced back to levels of normoxic controls (*$p<0.01$, n=7).

Media from OL cultures exposed to OGD showed significantly increased LDH levels compared to that from normoxic controls, as seen in FIG. 2 ($p<0.01$, $n=7$). Furthermore, HUCB cell treatment demonstrated oligoprotection. Media from OL cultures co-incubated with HUCB cells and subjected to OGD showed significantly reduced LDH levels relative to cultures subjected to OGD alone ($p<0.05$, $n=7$). Importantly, the fact that HUCB cells were separated from OLs by transwell inserts indicates that HUCB cells exerted these protective effects through the release of soluble factors rather than through direct cellular contact. The soluble factors were later identified to be leukemia inhibitory factor (LIF) and granulocyte colony stimulating factor. Thus, LDH levels in media from OL cultures co-incubated with HUCB cells during OGD were reduced relative to OL-only cultures.

Figure 3:
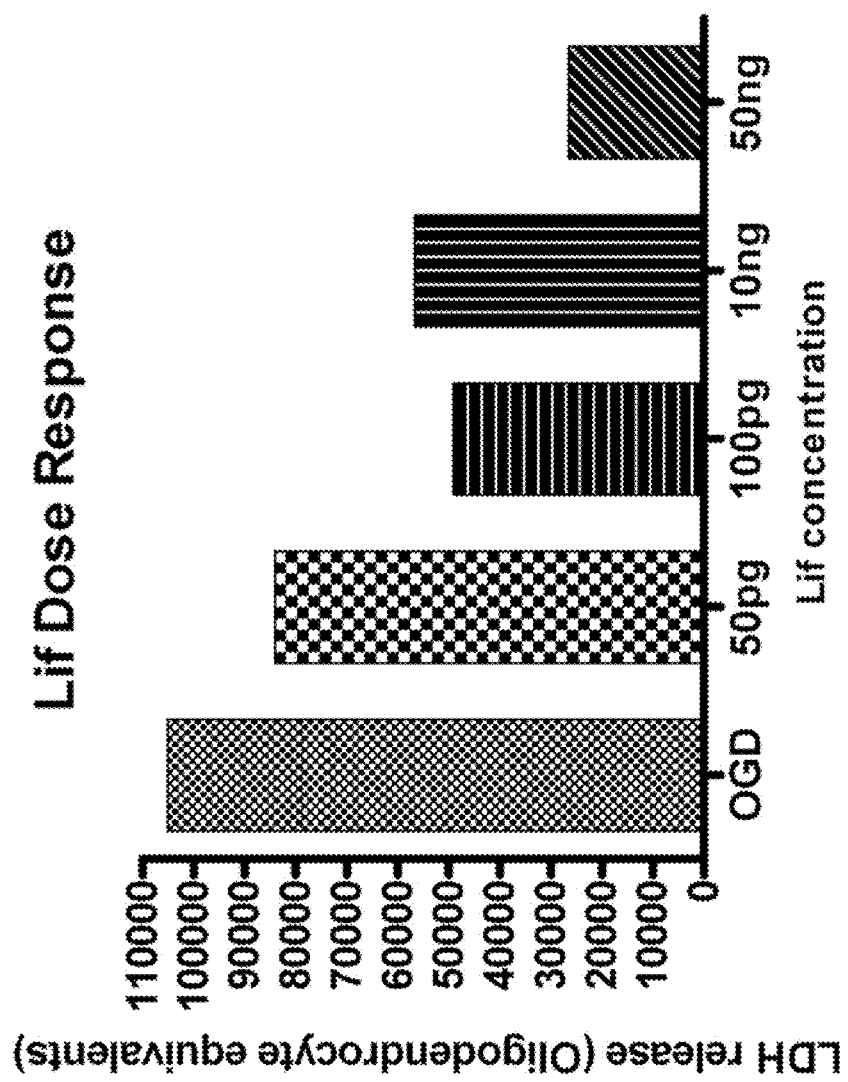
FIG. 3 is a graph showing tissue damage following ischemic conditions, without and with treatment of LIF at various concentrations.
Figure 4:
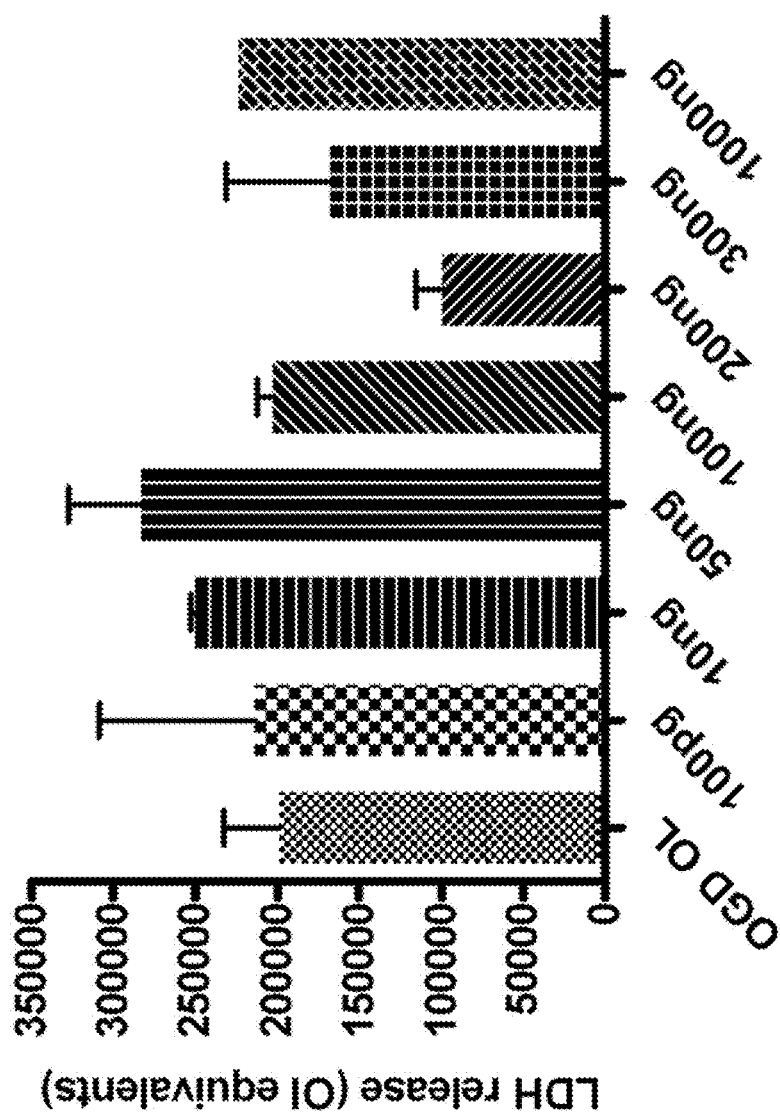
FIG. 4 is a graph showing tissue damage following ischemic conditions, without and with treatment of LIF at various concentrations.
Figure 5:
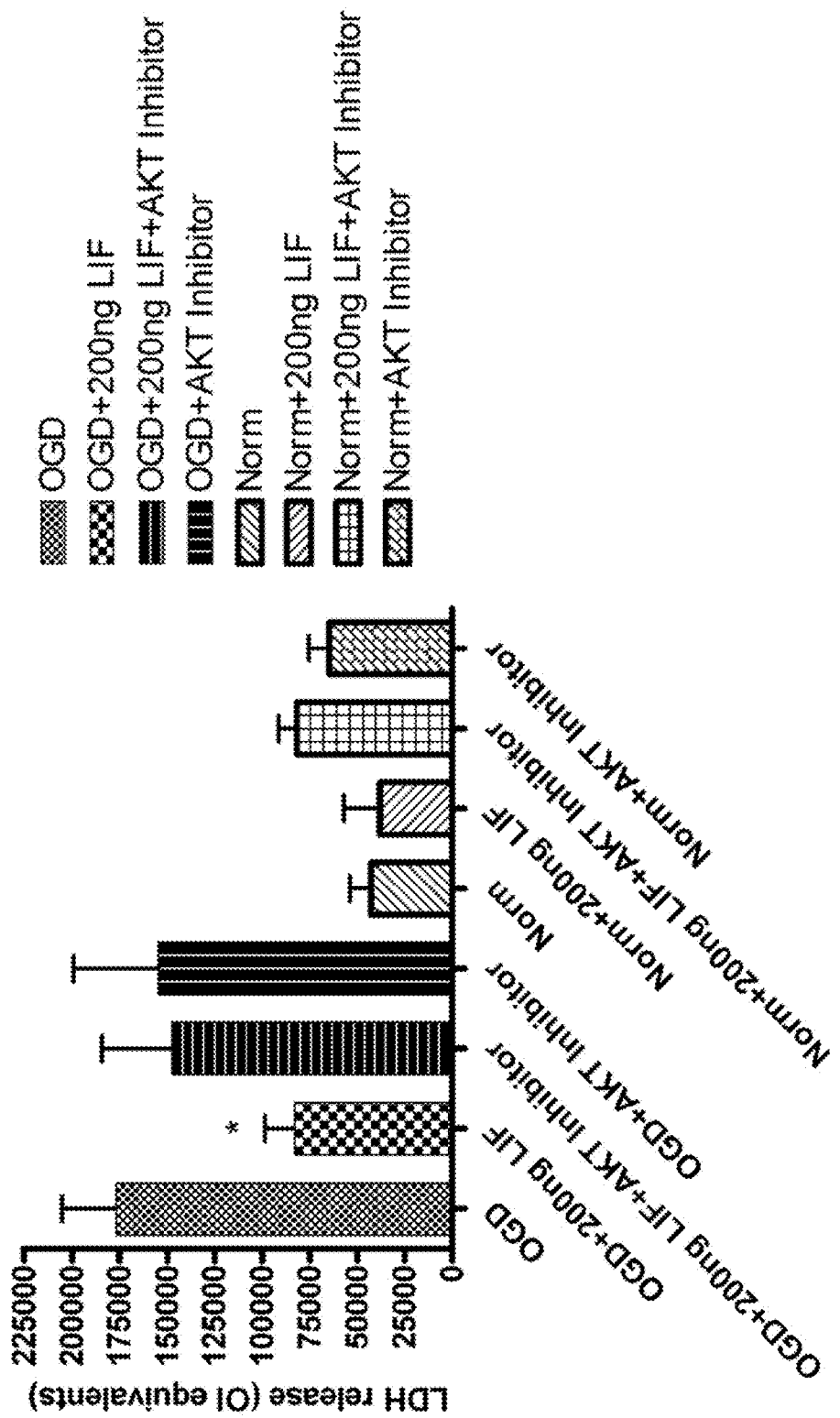
FIG. 5 is a graph showing tissue damage following ischemic conditions, without and with treatment of LIF at various concentrations and without and with AKT inhibitor, as compared to normoxic controls.
Figure 6:
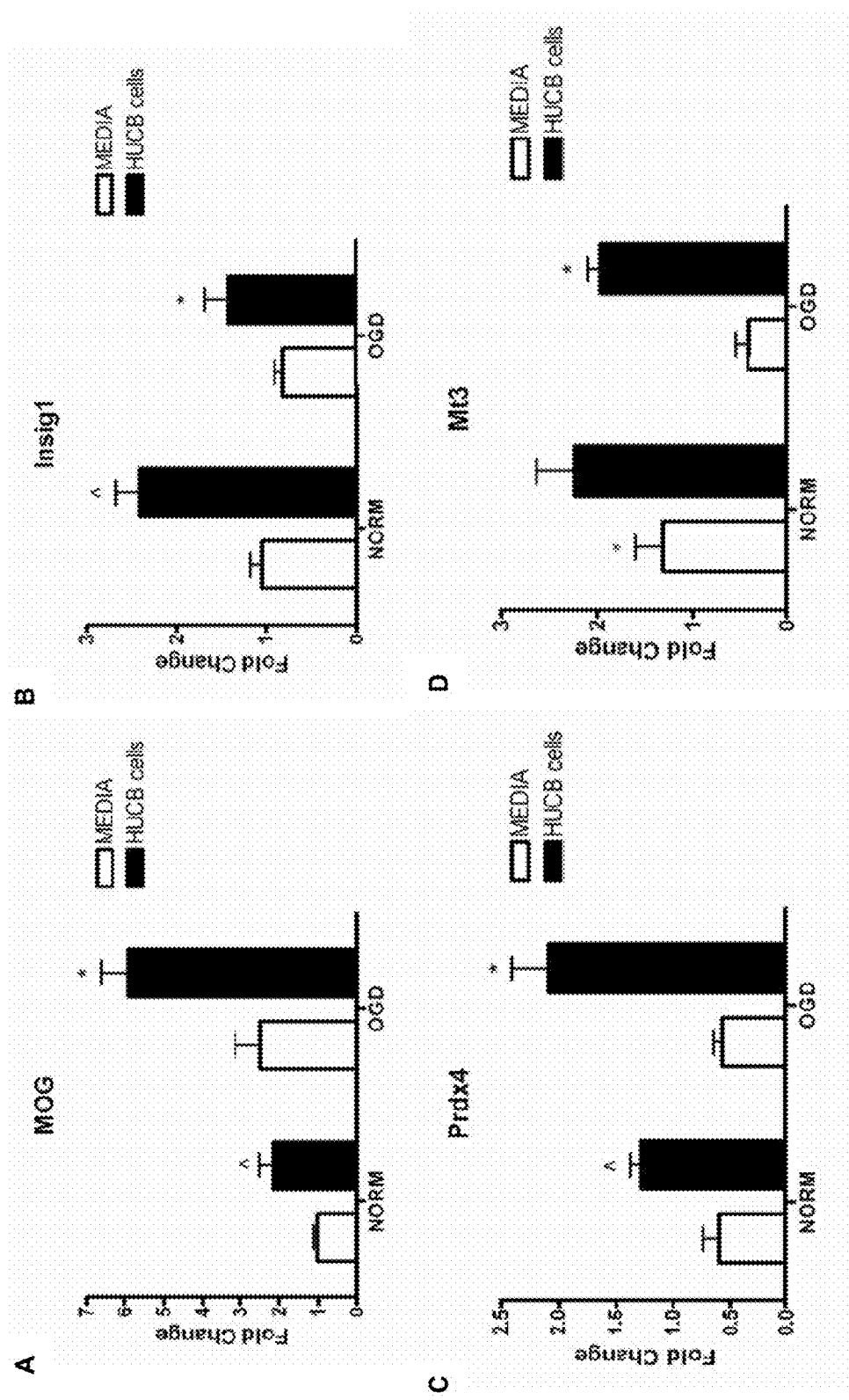
FIGS. 6(A) through (D) are graphs showing Affymetrix gene array fold changes are confirmed by qRT-PCR. HUCB cell treatment of OLs exposed to 24 hrs OGD significantly increased gene expression of (A) MOG, (B) Insig1, (C) Prdx4, and (D) Mt3, as compared to OLs subjected to OGD alone (*$p<0.05$, n=5). Additionally, HUCB cell treatment of OLs exposed to normoxia increased the expression of the respective protein as compared to non-treated normoxic controls (^ $p<0.05$ n=5). Under OGD conditions, OL expression of (D) Mt3 was significantly reduced in non-treated cells compared to both normoxic groups (# $p<0.05$, n=5).
Figure 7:
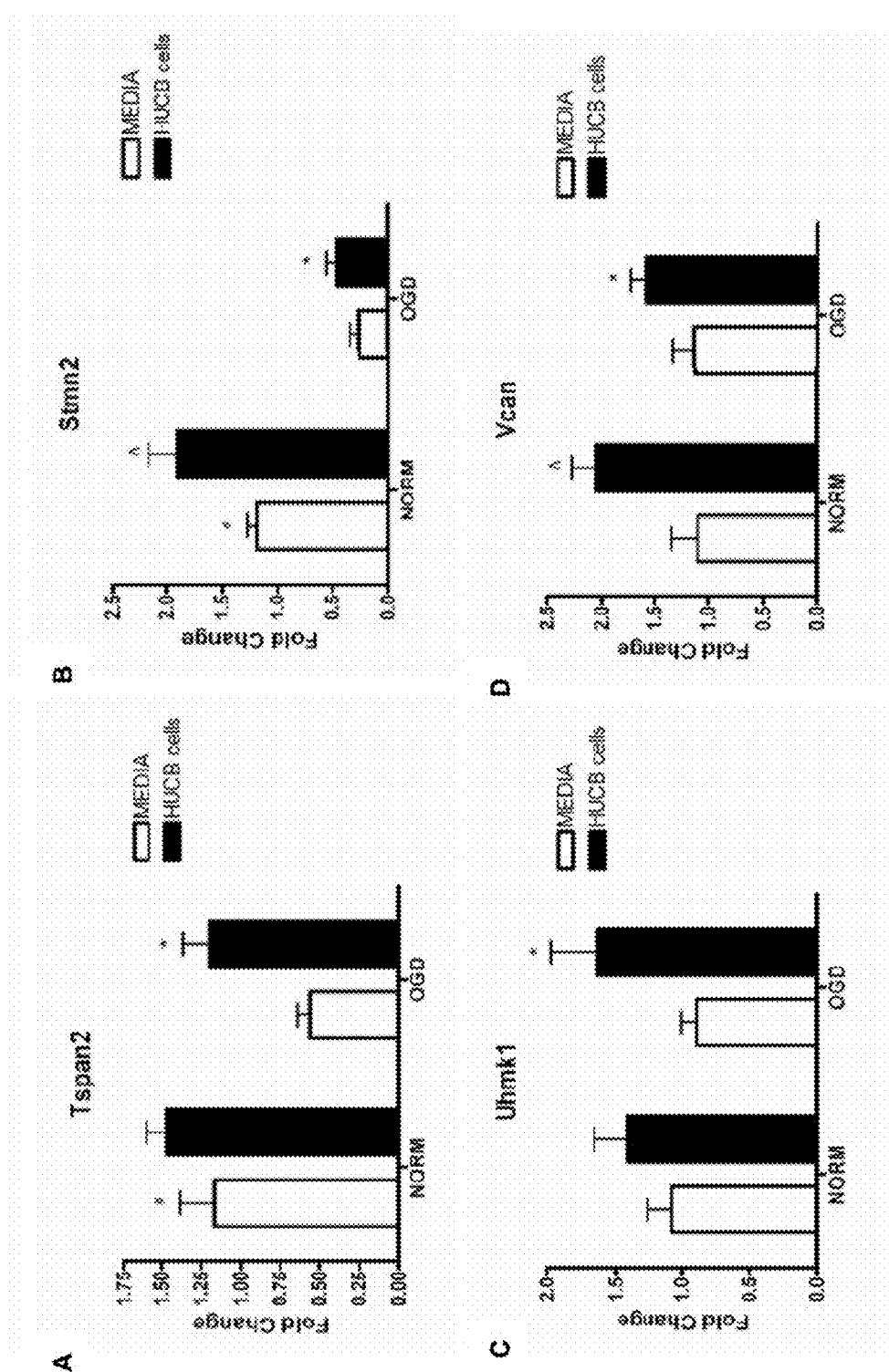
FIGS. 7(A) through (D) are graphs showing Affymetrix gene array fold changes are confirmed by qRT-PCR. HUCB cell treatment of OLs exposed to 24 hrs OGD significantly increased gene expression of (A) Tspan2, (B) Stmn2, (C) Uhmk1 and (D) Vcan as compared to OLs subjected to OGD alone (*$p<0.05$, n=5). Additionally, HUCB cell treatment of OLs exposed to normoxia increased the expression of the respective protein as compared to nontreated normoxic controls (^ $p<0.05$ n=5). Under OGD conditions, OL expression of (A) Tspan2 and (B) Stmn2 were significantly reduced in non-treated cells compared to both normoxic groups (# p<0.05, n=5).
Figure 8:
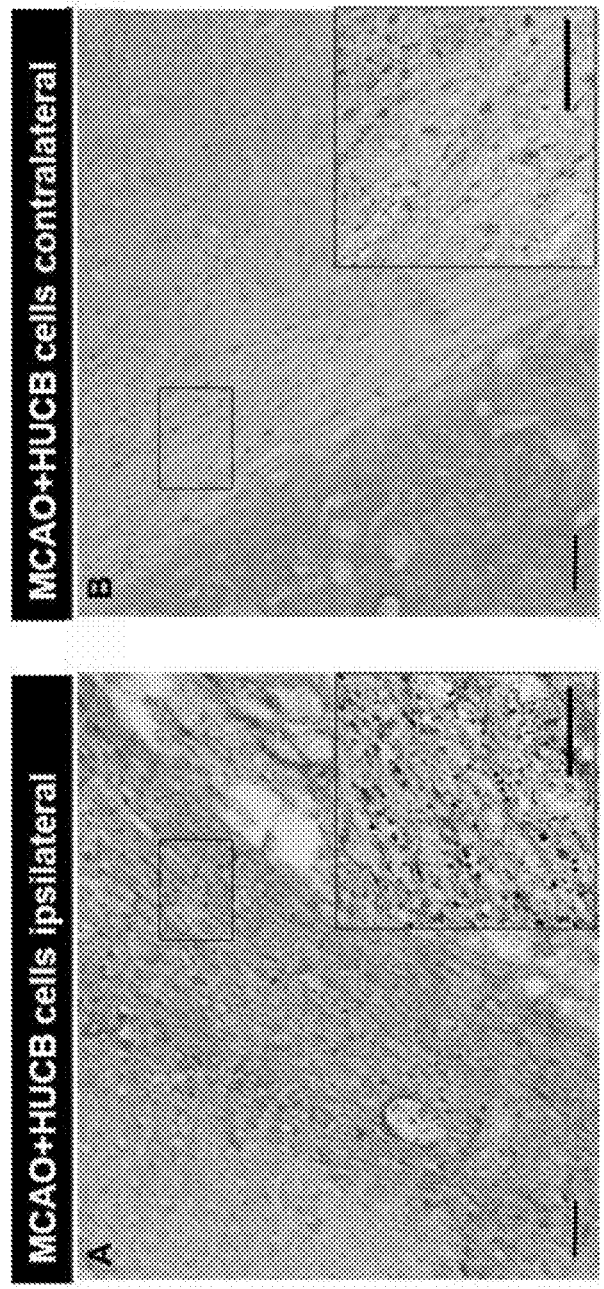
FIGS. 8(A) and (B) are images showing HUCB cells increase white matter Uhmk1 expression following ischemic insult. HUCB cell treatment in the (A) ipsilateral, and (B) contralateral hemispheres 48 hrs post-MCAO significantly increased Uhmk1 expression in the external capsule compared to vehicle (FIG. 6) and sham-operated (FIG. 7) controls (* p<0.05, n=3). Low magnification scale bars=100 μm; high magnification inset scale bars=20 μm.
Figure 9:
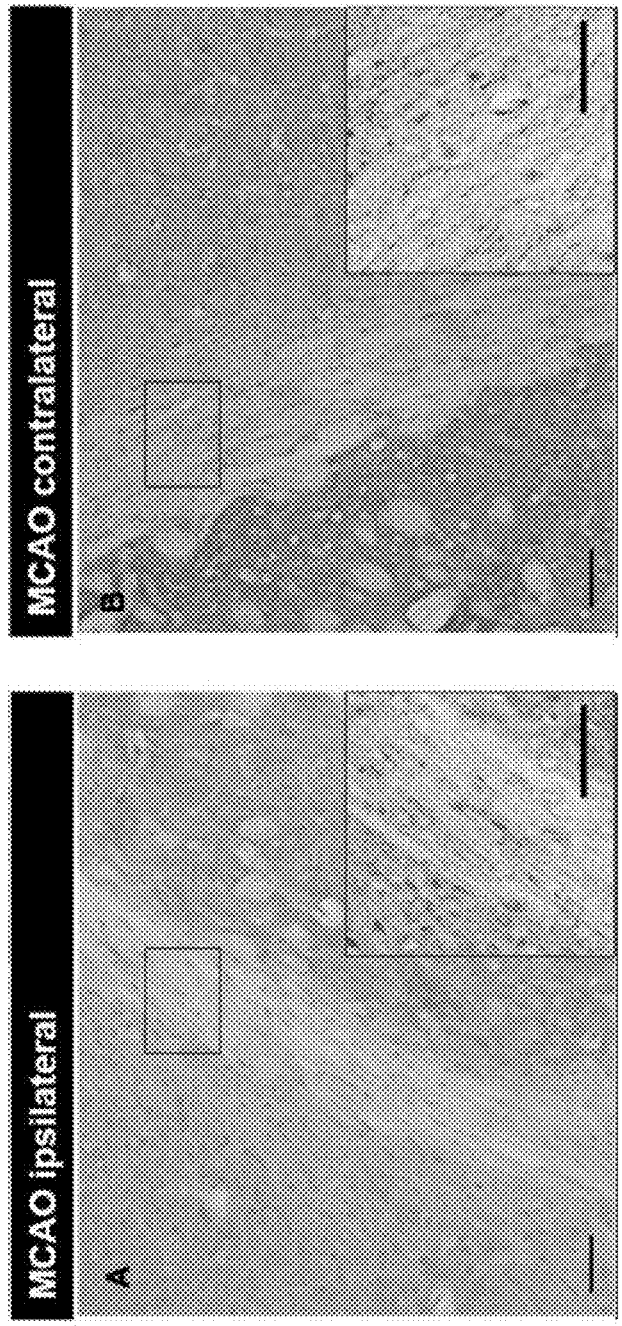
FIGS. 9(A) and (B) are images showing vehicle administration following ischemic insult for comparison to HUCB cell treatment (FIG. 5). Vehicle was administered to the (A) ipsilateral, and (B) contralateral hemispheres 48 hrs post-MCAO and show that HUCB cells increased Uhmk1 expression in the external capsule (* p<0.05, n=3). Low magnification scale bars=100 μm; high magnification inset scale bars=20 μm.
Figure 10:
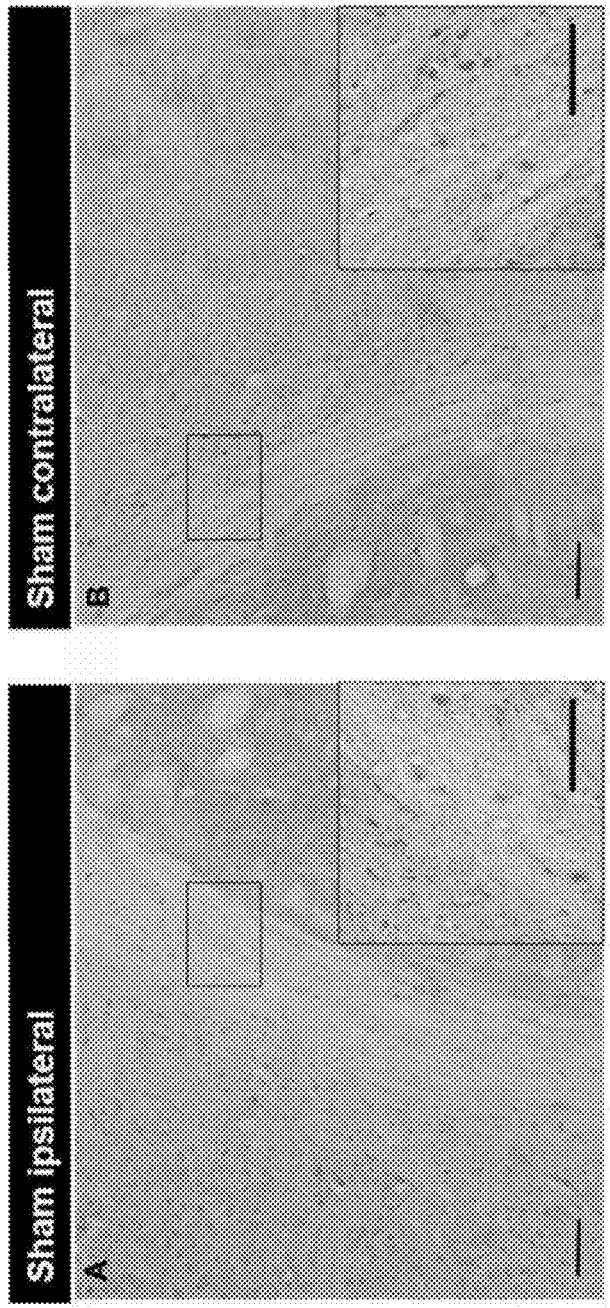
FIGS. 10(A) and (B) are images showing Sham-operated controls for comparison to HUCB cell treatment (FIG. 5). Sections were taken from the (A) ipsilateral, and (B) contralateral hemispheres 48 hrs post-sham MCAO surgery. Low magnification scale bars=100 μm; high magnification inset scale bars=20 μm.

Testing of LIF shows that this factor protects oligodendrocytes from oxygen glucose deprivation, as seen in FIGS. 3 and 4. An oxygen deprivation model was used to test the effect of LIF on primary rat oligodendrocyte cultures. Cells were grown in neurobasal medium containing B27 and 1.5 ml glutamine prior to OGD. To simulate ischemic conditions, the neurobasal medium was replaced with DMEM containing no glucose (OGD). The cells were then exposed to 1% $O_2$, 5% $CO_2$ and 94% $N_2$ for 24 hours. No LIF (OGD) or LIF was added to the cells, at the concentrations indicated. Increasing the amount of LIF results in a drop in extracellular LDH levels, to about 47.6% at 100 pg compared to untreated neurons (OGD). More impressively, at 50 ng, extracellular LDH is approximately 2.7% the amount of untreated cells. LIF's effects appear controlled by PI3K-AKT pathways, at least in part, as seen in FIG. 5. Therefore, systemic application of LIF at 48 hours post-injury as a therapy for stroke to protect white matter as well as gray matter.

Affymetrix microarray was utilized to detect changes in gene expression elicited by HUCB cells that were co-incubated with OLs during OGD. Gene array was performed by the H. Lee. Moffitt Cancer Center Microarray Core Facility utilizing a GeneChip 3000 Scanner, GCOS 1.4 with an Affymetrix MAS 5.0 algorithm to generate signal intensities, and GeneChip Rat Genome 230 2.0 Array (Affymetrix inc, Santa Clara, Calif.). Microarray data were normalized to RNA from cultures exposed to OGD. Only genes with ≥1.5 fold increase and a signal intensity of >100 were selected for further investigation. For investigated treatment groups, samples were pooled ($n=5$) to obtain the necessary RNA quantity and quality to perform this procedure.

HUCB cells showed neuroprotection via changes in OL gene expression. Of the 33 genes detected, eight genes encoding proteins associated with OL proliferation, survival, and repair functions were selected for further investigation, seen in Table 1, bold font: Uhmk1, Insig1, Mt3, Tspan2, Prdx4, Stmn2, MOG, and Vcan. Genes listed in Table 1 exclude expressed sequence tags and exhibit fold changes>1.5 compared to OGD controls.

TABLE 1

HUCB cell treatment alters gene expression in OLs subjected to 24 hrs OGD. OL genes for which HUCB cell treatment during IGD caused a fold change ≥1.5 compared to non-treated OGD controls. Genes were groups based on functional relevance, and those associated with OL survival, proliferation, and myelination (bold font) were selected for further investigation.

| Genes and Function | Fold Change |
|---|---|
| Antioxidant/Free Radical Scavenging | |
| Metallothionein 3 | 1.64 |
| Peroxiredoxin 4 | 5.27 |
| Lipid Biosynthesis. Myelination | |
| UDP galactosyltransferase 8A | 1.68 |
| Insulin-induced gene 1 | 1.71 |
| 3-hydroxy-3-methylglutaryl-Coenzyme A synthase 1 | 1.73 |
| Myelin Oligodendrocyte Glycoprotein | 1.92 |
| Isopentyl-diphosphate delta isomerase | 2.22 |
| Growth/Proliferation | |
| Rhoa | 1.62 |
| Crystallin, alpha B | 1.72 |
| U2AF homology motif (UHM) kinase 1 | 1.97 |
| Integrin-linked kinase | 1.99 |
| Guanine nucleotide binding protein, alpha o | 2.22 |
| Translin-associated factor X | 2.96 |
| S100 calcium binding protein A6 (calcyclin) | 3.54 |
| Ret proto-oncogene | 3.91 |
| Protein kinase C, beta 1 | 5.34 |
| Lumican | −5.73 |
| Pleckstrin homology-like domain, family A, member 1 | −20.77 |
| Structural | |
| Tetraspanin 2 | 1.54 |
| Actin related protein ⅔ complex, subunit 1A | 1.56 |
| Vimentin | 1.63 |
| Microtubule-associated protein tau | 1.72 |
| Actin related protein ⅔ complex, subunit 1B | 1.78 |
| Tropomyosin 1, alpha | 2.03 |
| Versican | 2.54 |
| Ral GEF with PH domain and SH3 binding motif 2 | 2.70 |
| Stathmin-like 2 | 2.73 |
| Microtubule-associated protein 2 | 5.50 |
| Metabolic | |
| Translocase of inner mitochondrial membrane 8 homolog b (yeast) | 1.67 |
| Translocase of inner mitochondrial membrane 10 homolog (yeast) | 1.73 |
| Acyl-CoA thioesterase 2 | −69.70 |
| Signaling | |
| Endothelial differentiation, lysophosphatidic acid G-protein-coupled receptor, 2 | 2.46 |
| Phospholipase D1 | 3.20 | qRT-PCR was performed to validate gene expression data obtained by microarray analysis. RNA was collected from supplementary experiments in which HUCB cell co-incubation rescued OLs subjected to 24 hrs OGD. Primers were ordered for selected sequences in which expression of genes deemed vital to OL survival and proliferation were increased at least 1.5-fold after HUCB cell treatment. Uhmk1, Insig1, Mt3, Tspan2, Prdx4, Stmn2, and MOG were purchased from SABiosciences (Frederick, Md.; sequences are proprietary). Vcan (Integrated DNA Technologies Coralville, Iowa) was examined using the following primers:

```
Reverse 5' TTT TAG GCA TTG CCC ATC TC    (SEQ ID 1)

Forward 5' ATG ACG TCC CCT GCA ACT AC    (SEQ ID 2)
```

Total RNA (10 ng/µl) from OL cultures were subjected to qRT-PCR. The RT reaction mixture consisted of 3 µl Oligo (dT) Primers, 10 µl cDNA Synthesis Master Mix (2×), 1 µl of Affinity Script RT/RNase Block enzyme mixture, and RNase-free H2O to a total volume of 20 µl (Stratagene, La Jolla, Calif.). The reaction was incubated at 25° C. for 5 min to allow primer annealing, then incubated at 42° C. for 45 min to allow cDNA synthesis followed by 5 min incubation at 95° C. to terminate the cDNA synthesis reaction.

Complementary DNA from the RT reaction was added to a PCR reaction mix consisting of 1 µl cDNA, 12.5 µl 2× Brilliant 490 SYBR Green QPCR Master Mix (Stratagene), 2 µl primer, and nuclease-free PCR grade H2O to a total volume of 25 µl. The samples were amplified using a BioRad ICycler (Bio-Rad Laboratories, Hercules, Calif.) with the following protocol: heating to 95° C. for 15 min followed by 40 cycles of 30 sec denaturation at 95° C., 30 sec annealing at 55° C., and 30 sec of elongation at 72° C. GADPH was selected as a reference gene and was used to calculate the mean normalized expression.

qRT-PCR confirmed results obtained by microarray, seen in FIGS. 6(A) through 7(D). HUCB cell treatment increased expression of all selected genes, as seen in FIGS. 6(A) through (H), when compared to OLs subjected to OGD without HUCB cell treatment (p<0.05). In addition, OGD reduced the expression of Mt3, Tspan2, and Stmn2, seen in FIGS. 6(D), 7(A), and 7(B), relative to normoxic controls (p<0.05). HUCB cells also increased the gene expression of MOG, Insig1, Prdx4, Mt3, Stmn2, and Vcan, seen in FIGS. 6(A) through (D), 7(B) and 7(D), under normoxic conditions when compared to normoxia only controls. Furthermore, a trend was also observed whereby HUCB cell treatment during OGD either maintained or increased mRNA expression levels relative to those of normoxic controls for all genes except Stmn2.

Comparison of Gene Promoter

The promoter regions of genes upregulated in OLs co-cultured with HUCB cells during OGD were explored by Genomatix software. Common transcription factor binding sites were identified and included: EVI1, MZF1, GATA1, NK6.1, PAX6, Sox-5, and SRF, as seen in Table 2. These results suggest that the genes identified by microarray are being transcriptionally elevated by similar signaling pathways activated by the soluble factors secreted from the HUCB cells.

TABLE 2

Common transcription factor binding sites present in the promoters of upregulated genes. Common transcription factor binding sites identified in the promoter regions of Prdx4, Mt3, Insig1, MOG, Uhmk1, Tspan2, Vcan, and Stmn2. 8/8 denotes transcription factor binding sites present in all 8 genes, whereas 7/8 denotes transcription factor binding sites present in 7 of the 8 selected genes.

| Transcription Factor 8/8 | Transcription Factor 7/8 |
|---|---|
| Ecotropic viral integration site 1 | Cut-like homeodomain protein (Cut Repeat 1) |
| Hepatic nuclear factor 1 | Homeodomain transcription factor Gsh-2 |
| Ribonucleoprotein associated zinc finger protein MOK-2 | CP2 erthrocyte factor related to *drosophila* Elf1 |
| Myeloid zinc finger protein MFZ1 | Myelin transcription factor 1-like, neuronal C2HC zinc finger factor 1 |
| Nuclear factor 1 | SWI/SNF related, matrix associated, actin dependent regulator of chromatin, subfamily a, member 3 |
| NK6 homeobox 1 | |
| Pax-6 paired domain binding site | SRY (sex determining region Y)-box 5 |
| Proximal sequence element (PSE) of RNA Polymerase III- transcribed genes GATA-binding factor 1 | Stimulating protein 1, ubiquitous zinc finger transcription factor Serum response factor |

For fluorescent labeling, cultured OLs were lifted and washed with PBS for 5 min and incubated in 3% hydrogen peroxide for 20 min, except for fluorescence samples which were not incubated in hydrogen peroxide. The cells were washed 3 times in PBS, incubated for 1 hr in permeabilization buffer (2% serum, 0.3% Triton X-100 and 0.3% 1M lysine in PBS) and incubated overnight at 4° C. with primary antibody in antibody solution (2% goat serum, 0.3% Triton X-100 in PBS). The following day, sections were washed with PBS. Double-label immunohistochemistry was achieved by co-incubating the tissues or cells with primary antibodies raised in two distinct species, followed by co-incubation with secondary antibodies conjugated to distinct fluorophores. Following secondary antibody incubation, sections were washed and cover-slipped using VectaShield Hard Set with DAPI (Vector Laboratories). Antibodies used for fluorescent detection consisted of the following: mouse anti-RIP (Millipore, Temecula, Calif.; 1-5000), rabbit anti-Prdx4 (Abcam; 1:500), mouse anti-O4 (Chemicon, Temecula, Calif.; 1:1000), mouse anti-OX-42 (AbD Serotec, Kidlington, Oxford, UK; 1:1000), rat anti-MBP (Abcam; 1:1000), rabbit anti-NG2 (Chemicon; 1:500), rabbit anti-Uhmk1 (Protein tech group; 1:50), goat anti-Insig1 (Santa Cruz Biotechnology Inc; 1:50), rabbit anti-Mt3 (Sigma-Aldrich; 1:50), and mouse anti-GFAP (Chemicon; 1:1000). Secondary antibodies used were Alexa Fluor 488 and 594 (Molecular Probe, Eugene, Oreg.; 1:1000). Negative controls were labeled in the absence of primary antibody corresponding with respective secondary, as discussed previously.

Figure 11:
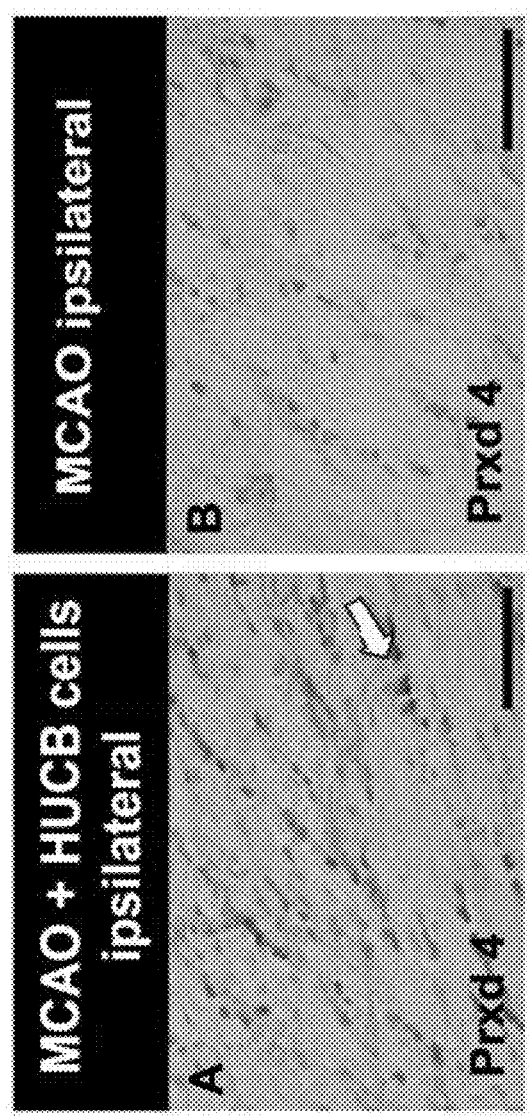
FIGS. 11(A) and (B) show HUCB cells alter white matter protein expression following ischemic insult. Photomicrographs show increased expression of Prdx4 in the ipsilateral hemisphere of animals treated with HUCB cells 48 hrs post-MCAO for (A) HUCB cell-treated animals and (B) vehicle-treated controls. Scale bars=50 μm. Arrows points to positive staining.
Figure 12:
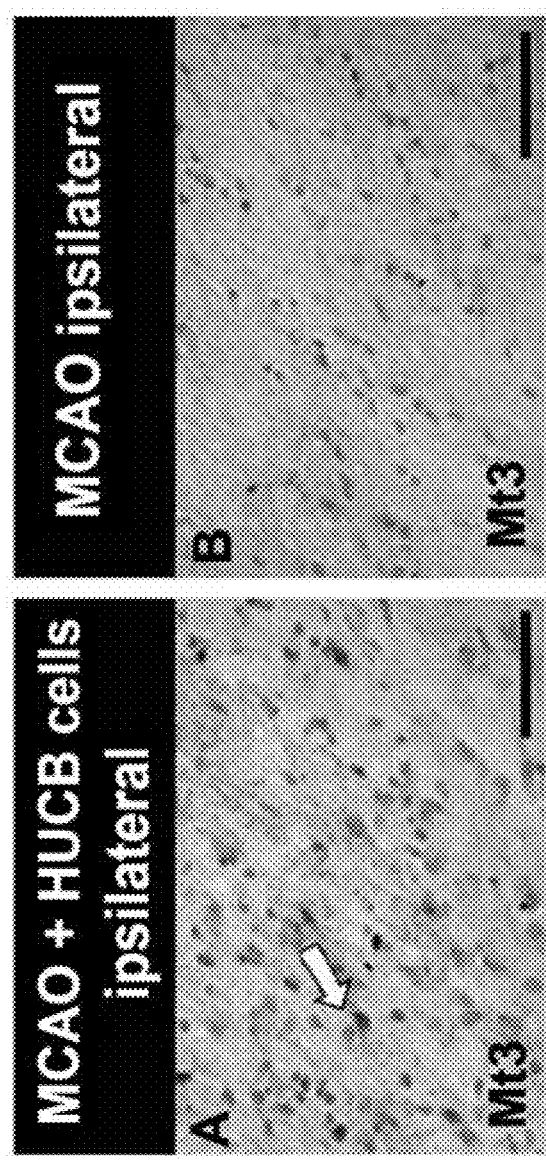
FIGS. 12(A) and (B) show HUCB cells alter white matter protein expression following ischemic insult. Photomicrographs show increased expression of Mt3 in the ipsilateral hemisphere of animals treated with HUCB cells 48 hrs post-MCAO for (A) HUCB cell-treated animals and (B) vehicle-treated controls. Scale bars=50 μm. Arrows points to positive staining.
Figure 13:
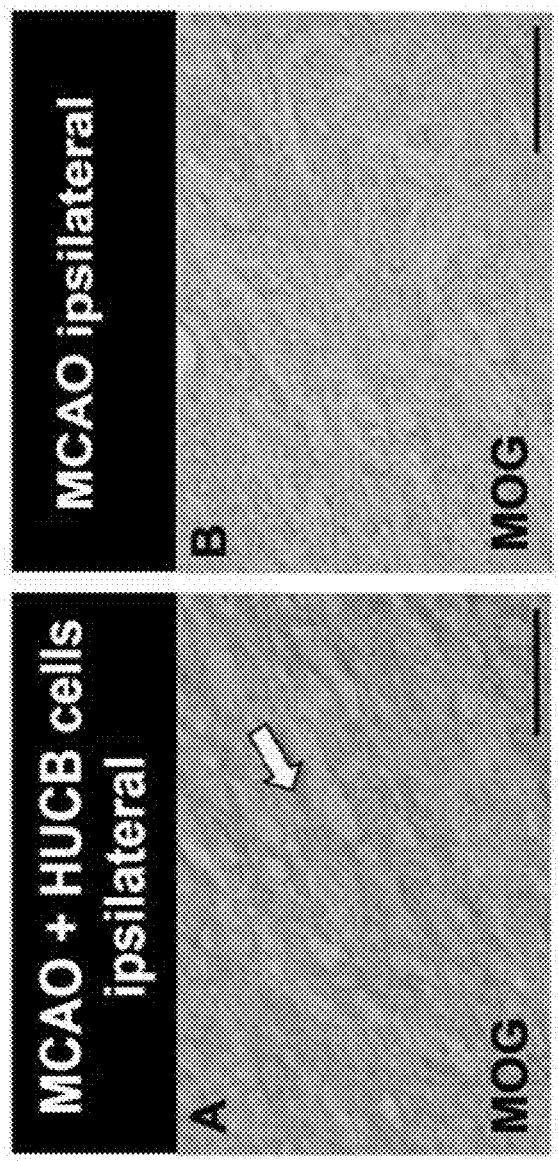
FIGS. 13(A) and (B) show HUCB cells alter white matter protein expression following ischemic insult. Photomicrographs show increased expression of MOG in the ipsilateral hemisphere of animals treated with HUCB cells 48 hrs post-MCAO for (A) HUCB cell-treated animals and (B) vehicle-treated controls. Scale bars=50 μm. Arrows points to positive staining.
Figure 14:
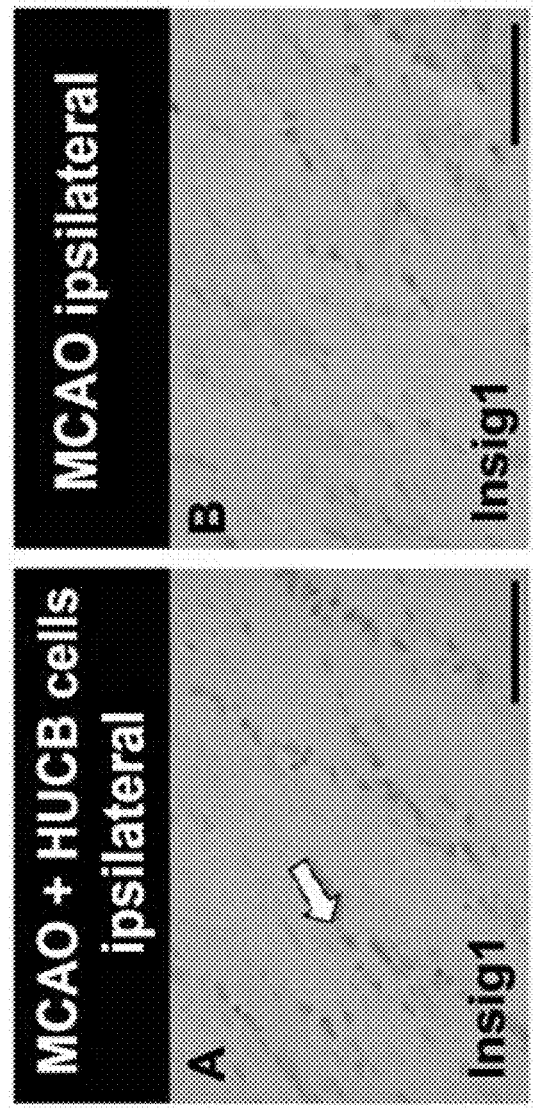
FIGS. 14(A) and (B) show HUCB cells alter white matter protein expression following ischemic insult. Photomicrographs show increased expression of Insig1 in the ipsilateral hemisphere of animals treated with HUCB cells 48 hrs post-MCAO for (A) HUCB cell-treated animals and (B) vehicle-treated controls. Scale bars=50 μm. Arrows points to positive staining.
Figure 15:
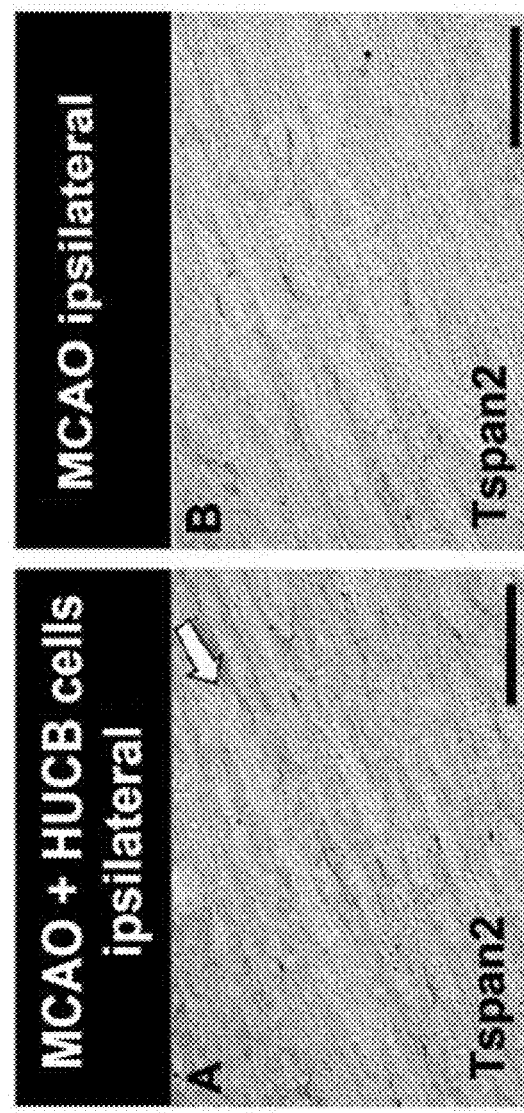
FIGS. 15(A) and (B) show HUCB cells alter white matter protein expression following ischemic insult. Photomicrographs show increased expression of Tspan2 in the ipsilateral hemisphere of animals treated with HUCB cells 48 hrs post-MCAO for (A) HUCB cell-treated animals and (B) vehicle-treated controls. No differences were observed in the expression of Tspan in response to HUCB cell treatment. Scale bars=50 μm. Arrows points to positive staining.
Figure 16:
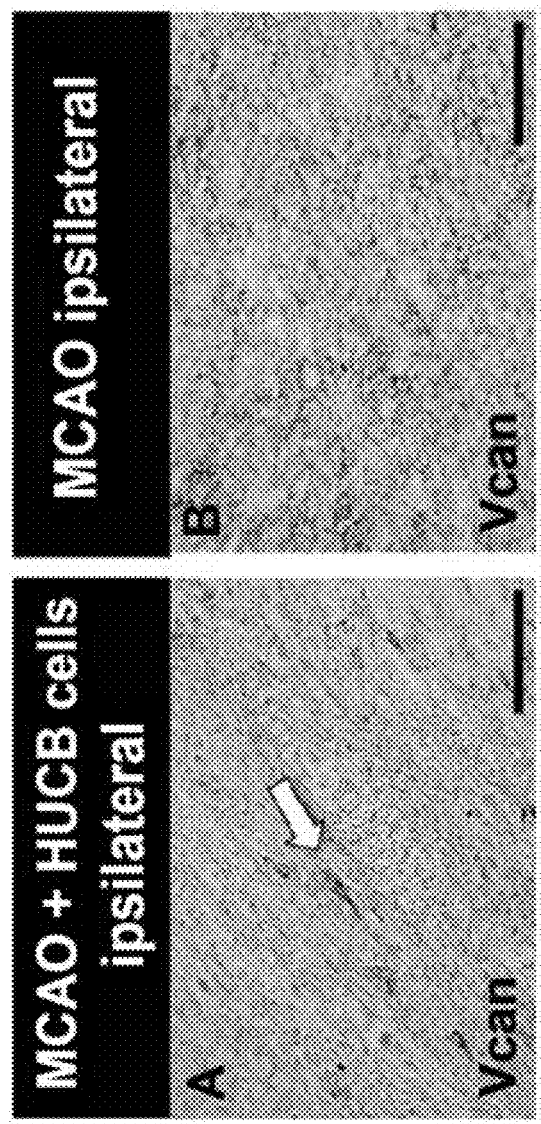
FIGS. 16(A) and (B) show HUCB cells alter white matter protein expression following ischemic insult. Photomicrographs show increased expression of Vcan in the ipsilateral hemisphere of animals treated with HUCB cells 48 hrs post-MCAO for (A) HUCB cell-treated animals and (B) vehicle-treated controls. No differences were observed in the expression of Vcan in response to HUCB cell treatment. Scale bars=50 μm. Arrows points to positive staining.
Figure 17:
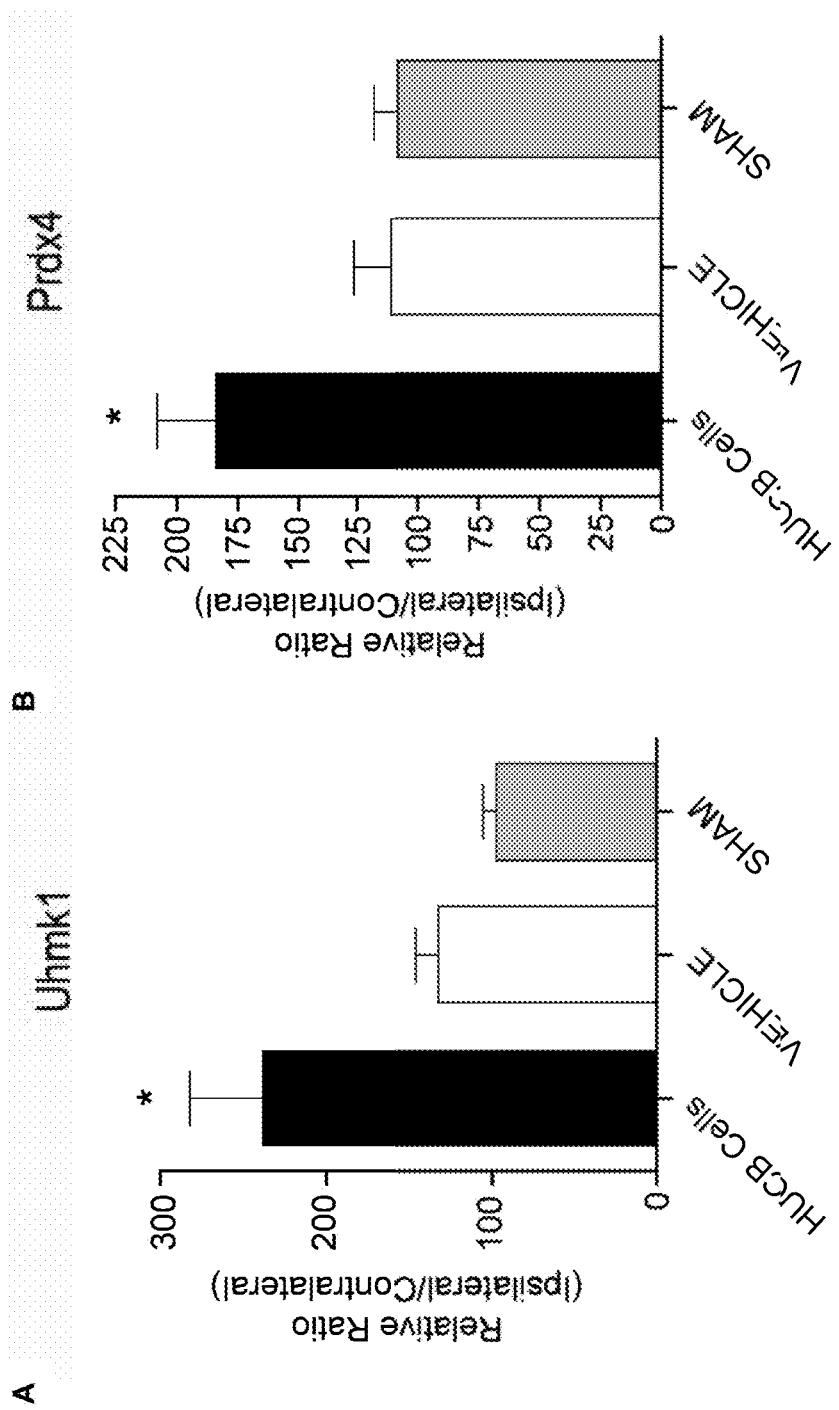
FIGS. 17(A) and (B) are graphs showing immunohistochemical quantification of white matter protein expression. HUCB cell treatment 48 hrs post-MCAO resulted in increased expression of (A) Uhmk1 and (B) Prdx4 in the ipsilateral external capsule compared to vehicle-treated and sham-operated.
Figure 18:
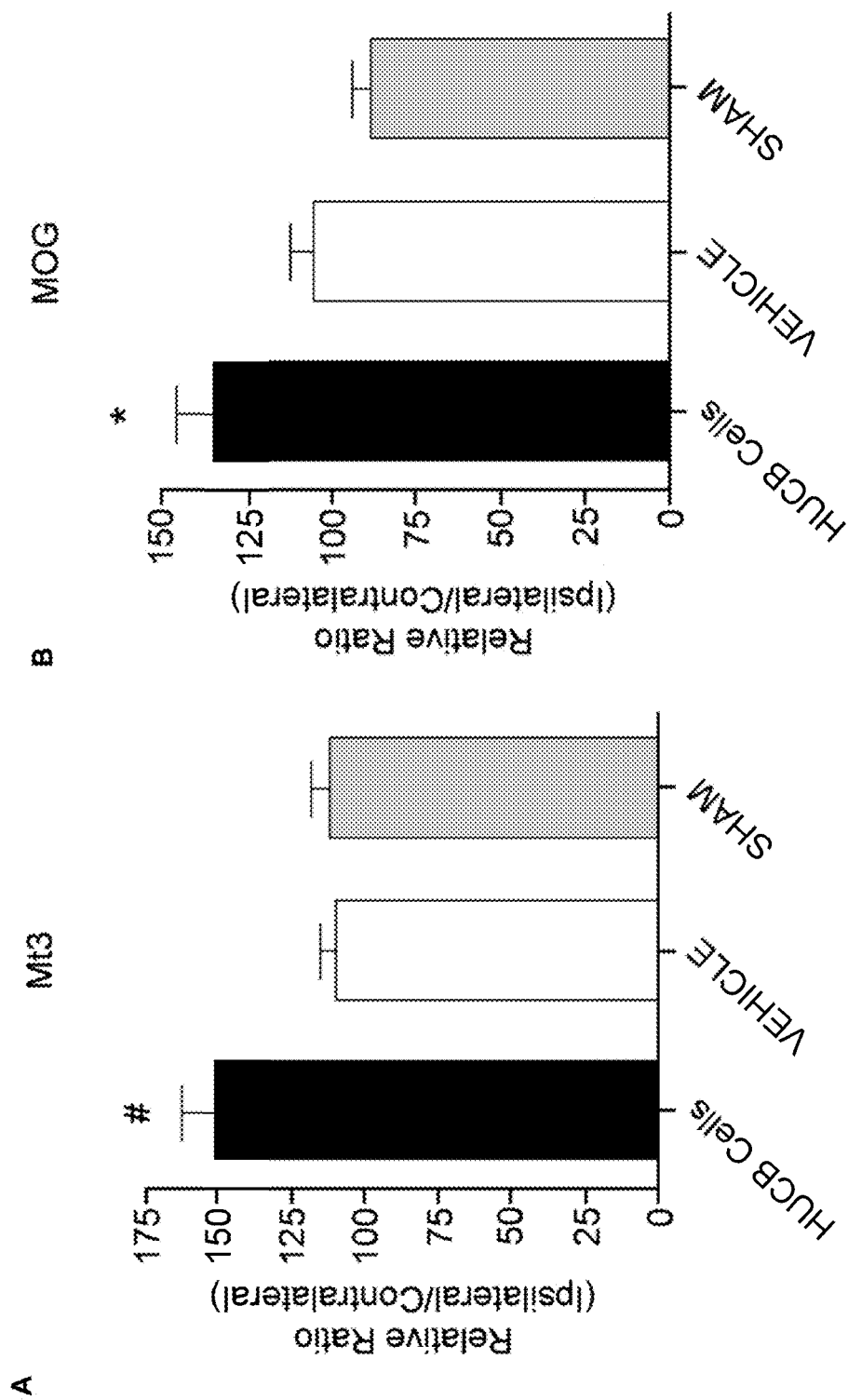
FIGS. 18(A) and (B) are graphs showing immunohistochemical quantification of white matter protein expression. HUCB cell treatment 48 hrs post-MCAO resulted in increased expression of (A) Mt3 and (B) MOG in the ipsilateral external capsule compared to vehicle-treated and sham-operated.
Figure 19:
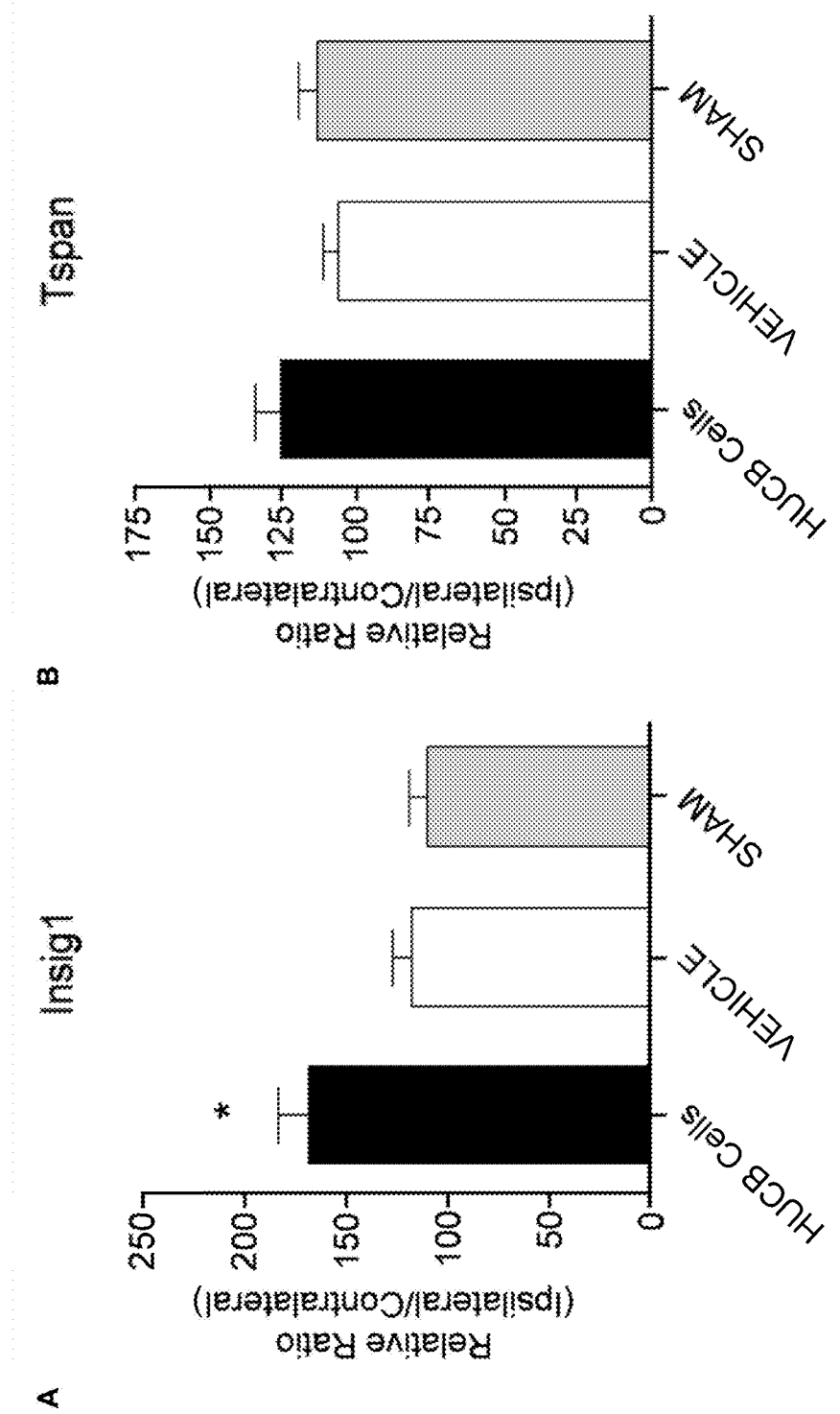
FIGS. 19(A) and (B) are graphs showing immunohistochemical quantification of white matter protein expression. HUCB cell treatment 48 hrs post-MCAO resulted in increased expression of (A) Insig1 and (B) Tspan2 in the ipsilateral external capsule compared to vehicle-treated and sham-operated.
Figure 20:
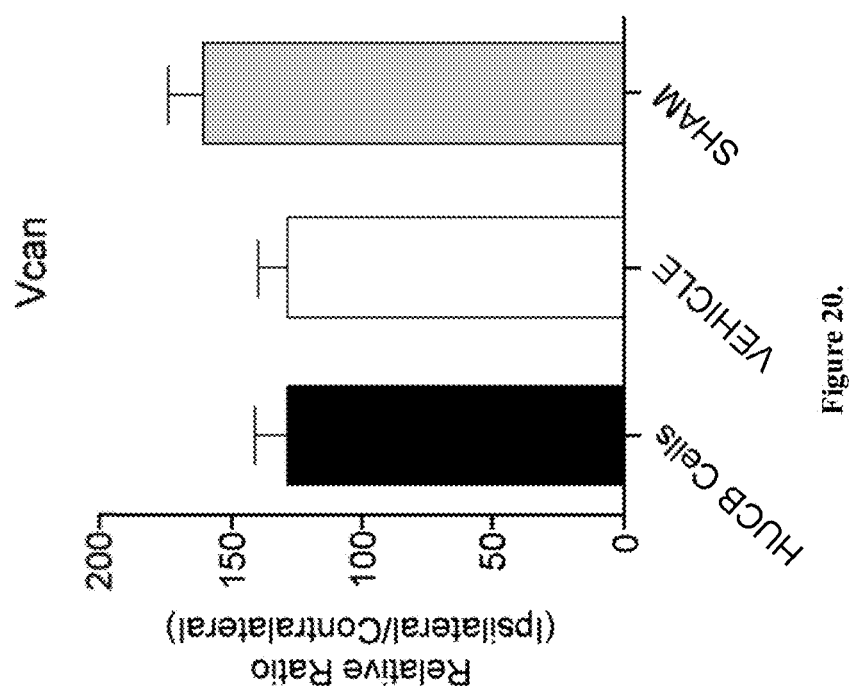
FIG. 20 is a graph showing immunohistochemical quantification of white matter protein expression in the contralateral hemisphere, as an internal control for the ipsilateral hemisphere. HUCB cell treatment 48 hrs post-MCAO did not result in significant expression differences in Vcan compared to vehicle-treated and sham-operated.
Figure 21:
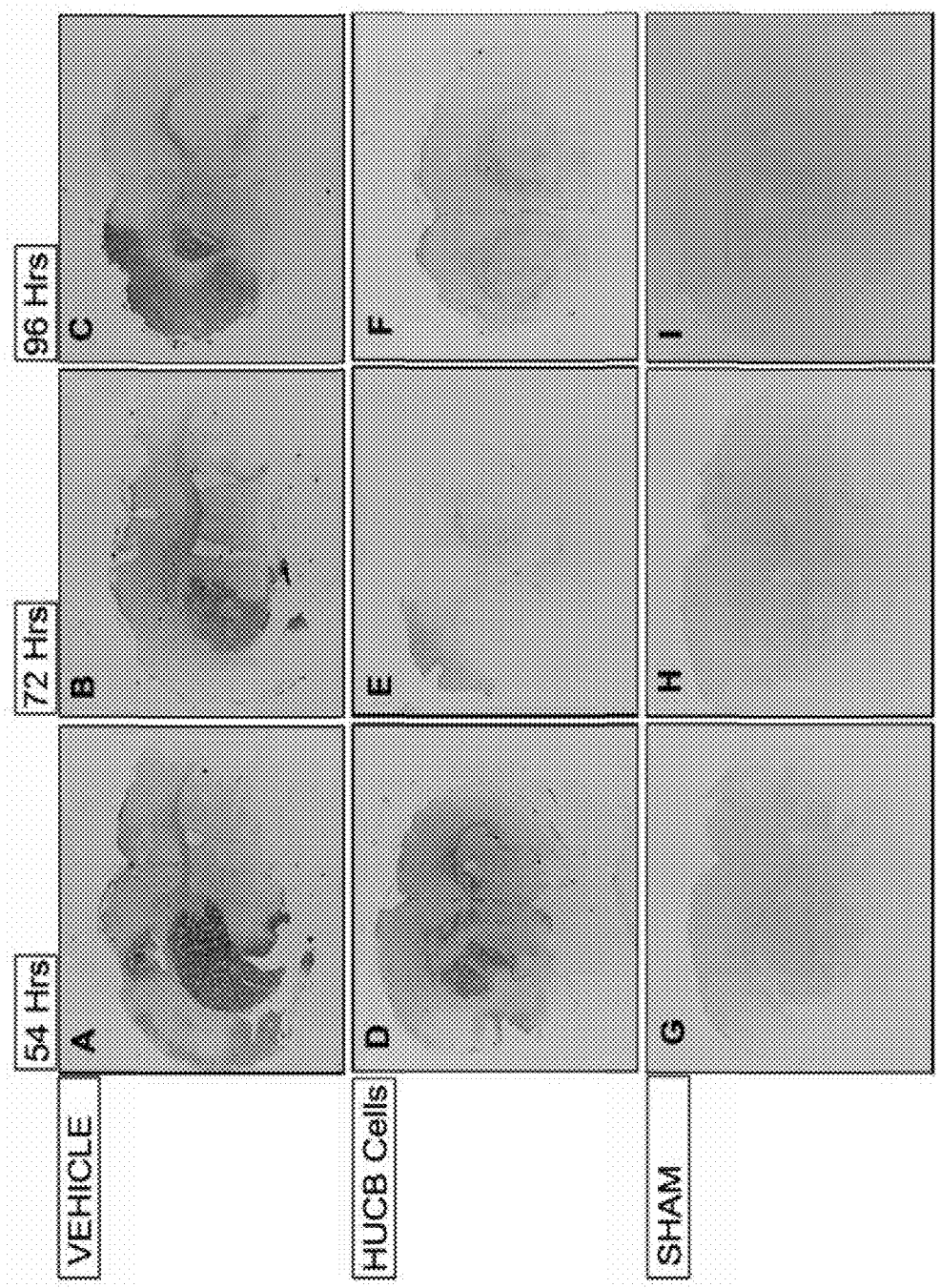
FIGS. 21(A) through (I) are images showing HUCB cells reduce infarct volume. HUCB cells provide neuroprotection when given systemically 48 hrs post-stroke. Photomicrographs depict Fluoro-Jade staining of coronal rat brain sections at time points 54, 72 and 96 hrs post-MCAO. Infarct volume remained constant in MCAO only groups at (A) 54 hrs, (B) 72 hrs, and (C) 96 hrs post-MCAO. Whereas HUCB cell administration reduced infarct volume at (E) 72 hrs and (F) 96 hrs post-stroke while not significantly different from sham operated animals at (G) 54 hrs, (H) 72 hrs, and (I) 96 after sham surgery (p>0.05).
Figure 22:
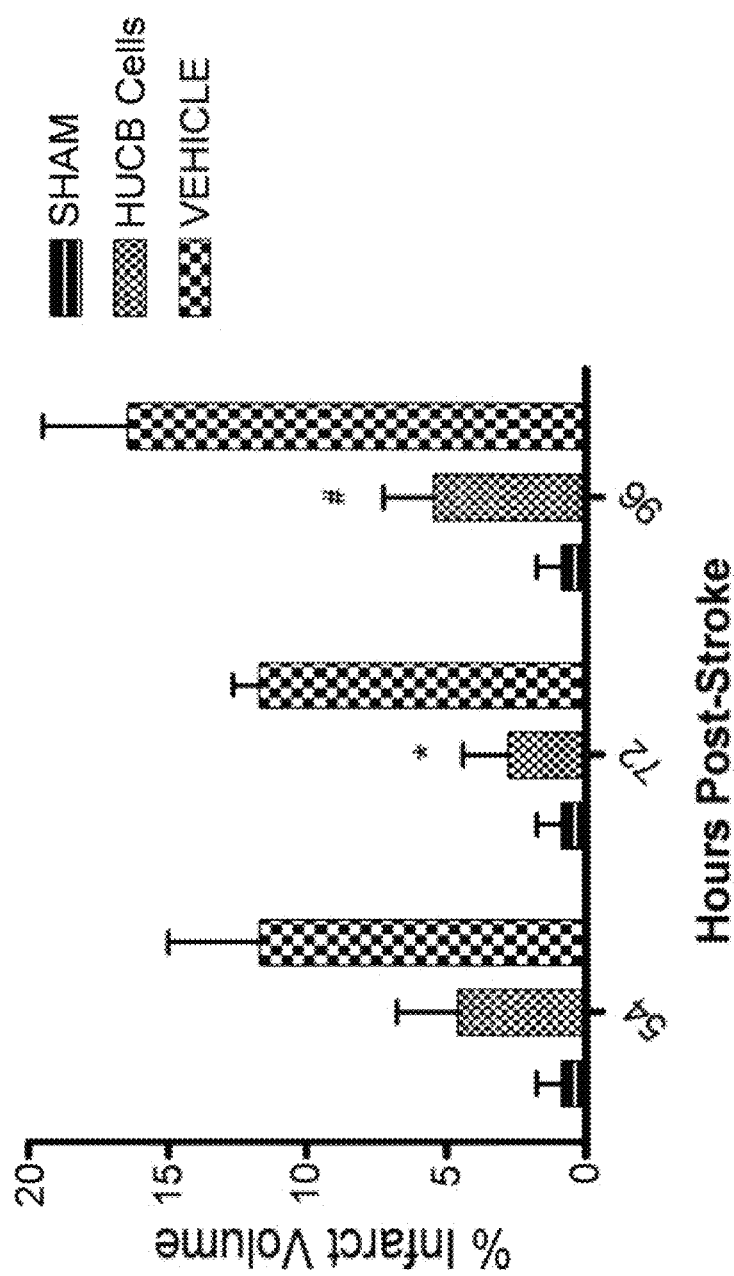
FIG. 22 is a graph showing HUCB cells reduce infarct volume. The percent volume quantification of the ipsilateral (stroked) hemisphere compared to the contralateral (non-stroked) hemisphere are shown for 54 hrs, 72 hrs, and 96 hrs post-MCAO for HUCB cell-treated, vehicle-treated, and sham operated animals (*p<0.05, # p<0.01, respectively n=4).

To expand on the microarray data from OL cultures, immunohistochemistry was performed to determine whether increased OL gene expression in vitro was consistent with increased gene product expression in vivo, discussed below, in the white matter rich region of the external capsule, selected regions seen in FIG. 8(A) through 10(B). Experiments included sections from rats that were administered either vehicle or HUCB cells 48 hrs post-MCAO, and rats that were subjected to sham-MCAO and received vehicle injections. Immunostaining was performed for the following proteins: Uhmk1, seen in FIGS. 8(A) though 10(B), Prdx4, seen in FIGS. 11(A) and (B), Mt3, seen in FIGS. 12(A) and (B), MOG, seen in FIGS. 13(A) and (B), Insig1, seen in FIGS. 14(A) and (B), Tspan2, seen in FIGS. 15(A) and (B), and Vcan, seen in FIGS. 16(A) and (B). In general, sham-operated controls, seen in FIGS. 10(A) and (B), showed nearly identical staining patterns as vehicle-treated controls, seen in FIGS. 9(A) and (B), with no apparent differences in the expression of any proteins examined. While MOG, seen in FIGS. 13(A) and (B), and Vcan, seen in FIGS. 16(A) and (B), immunoreactivity was present throughout the extracellular space, immunoreactivity for all other proteins was restricted to cell bodies. Quantification was performed by calculating the mean percent area for each treatment group, seen in FIGS. 17(A) through 20. The contralateral hemisphere was utilized as an internal control to adjust for ipsilateral brain swelling caused by edema. There was no significant difference in the expression of any proteins when comparing sham-operated and vehicle-treated controls. Uhmk1, seen in FIG. 17(A), Prdx4, seen in FIG. 17(B), Mt3, seen in FIG. 18(A), MOG, seen in FIG. 18(B), and Insig1, seen in FIG. 19(A), were upregulated in rats treated with HUCB cells compared to sham-operated and vehicle-treated controls (*$p<0.05$, #$p<0.01$), while Tspan2, seen in FIG. 19(B), and Vcan, seen in FIG. 20, expression were unchanged.

Based upon these data, further experiments were conducted to identify the mechanisms by which HUCB cells confer protection. Gene expression analysis of OL cultures subjected to OGD and treated with HUCB cells revealed increased mRNA content of Uhmk1, MOG, Insig1, Mt3, Tspan2, Prdx4, Stmn2, and Vcan. Additionally, the levels of Mt3, Prdx4, MOG, Insig1 and Uhmk1 gene products were elevated in the ipsilateral external capsule of animals administered HUCB cells 48 hrs after MCAO. Previous reports have demonstrated expression of these proteins in OLs (Jin, M. H., et al., 2005. Characterization of neural cell types expressing peroxiredoxins in mouse brain. Neurosci Lett. 381, 252-7; Kursula, P., 2008. Structural properties of proteins specific to the myelin sheath. Amino Acids. 34, 175-85; Miyazaki, I., et al., 2002. Age-related changes in expression of metallothionein-III in rat brain. Neurosci Res. 43, 323-33; Sim, F. J., et al., 2008. Statin treatment of adult human glial progenitors induces PPAR gamma-mediated oligodendrocytic differentiation. Glia. 56, 954-62). Here, double-label immunohistochemistry showed that the OL-specific antibody RIP colocalizes with Prdx4, Mt3, Insig1 and Uhmk1 whereas only Prdx4 colocalized with astrocytes, while none of the proteins colocalized with microglia/macrophages. Both the increased gene expression in culture and the lack of colocalization with other glial cell types in vivo demonstrates that HUCB cells injected into MCAO rats caused OLs seated within the cerebral white matter to upregulate these proteins.

Example 2

Male Sprague-Dawley rats, weighing 300-350 g, were used subjected to middle carotid artery occlusion (MCAO) (Butler, T. L., et al., 2002. Neurodegeneration in the rat hippocampus and striatum after middle cerebral artery occlusion. Brain Res. 929, 252-60; Hall, A. A., et al., 2009. Human umbilical cord blood cells directly suppress ischemic oligodendrocyte cell death. J Neurosci Res. 87, 333-41; Vendrame, M., et al., 2004. Infusion of human umbilical cord blood cells in a rat model of stroke dose-dependently rescues behavioral deficits and reduces infarct volume. Stroke. 35, 2390-5) to test HUCB cell effects on oligodendrocytes. Prior to MCAO surgery, animals were anesthetized with 5% isofluorane/O2 in an induction chamber. Rats were treated prophylactically with Ketoprofen (10 mg/kg s.c.), atropine (0.25 mg/kg s.c.) and Baytril (20 mg/kg i.m.) in accordance with IACUC guidelines. Ketoprofen injections were continued 3 days post-MCAO to minimize pain and discomfort. A constant flow of anesthesia was supplied with an interfaced scavenging system (3-4% isofluorane, flow rate 1 L/min) throughout the procedure. For Doppler insertion, the head was shaved and an incision was made lateral to the midline of the dorsal plates of the skull. The skin was spread and tissue covering the skull bone was pushed aside with a cotton-tipped applicator. Using a micro-drill, a small hole was drilled into the skull at 1 mm posterior and 4 mm lateral to bregma. A hollow stainless steel guide screw was positioned into the hole and a fiber optic filament (500 m) was inserted through the screw guide and secured with Vetbond (3M, St. Paul, Minn.). Blood perfusion in the brain was monitored using the Moor Instruments (Devon, England) Ltd laser Doppler with Moor LAB proprietary Windows-based software. When surgery was complete, the screw guide was removed, bone wax placed in the burr hole and the scalp incision was sutured. Rats that did not show>60% reduction in blood perfusion during MCAO were excluded from the study (Hall, A. A., et al., 2009. Human umbilical cord blood cells directly suppress ischemic oligodendrocyte cell death. J Neurosci Res. 87, 333-41).

Following implantation of the Doppler probe, the external carotid artery was exposed and isolated from the vagus nerve using blunt dissection. The artery was then ligated and transected near the bifurcation of the internal and external carotid arteries. The stump of the external carotid was then used as a guide to advance a monofilament through the internal carotid to the origin of the middle cerebral artery. The filament was then sutured secure and the incision closed. For sham surgeries, the Doppler probe was inserted and the external carotid exposed, but no filament inserted.

To determine whether HUCB cells were protective against stroke-induced injury, rats were injected (i.v., penile vein) with either HUCB cells (1×106 HUCB cells in 500 PBS (pH 7.4+DNase) or vehicle (500 µL, PBS+DNase only) 48 hrs after MCAO surgery. Sham-operated animals also received vehicle. Animals were then sacrificed 54, 72, and 96 hrs post-stroke and transcardially perfused with 0.9% NaCl followed by 4% paraformaldehyde in PBS. The brains were removed and saturated with 4% paraformaldehyde in PB followed by increasing concentrations of sucrose in PBS (20%, 30%). Brains were then sectioned at 30 µm on a cryostat to include bregma 1.7 mm through bregma −3.3, thaw mounted onto slides and stored at −20° C.

Brain sections were subjected to Fluoro-Jade analysis. Sections were thawed, dried and rehydrated with 100% EtOH for 3 min, 70% EtOH for 1 min, and 1 min in ddH2O. Using a 0.06% KMnO4 solution, sections were oxidized for 15 min. After 3×1 min washes in ddh20, brain sections were placed in a 0.001% solution of Fluoro-Jade (Histochem, Jefferson, Ark.) in 0.1% acetic acid for 30 min. Following incubation, sections were washed 4×3 min in ddH2O, dried, cleared in xylene, and cover-slipped with DPX mounting medium (VWR International Ltd, Poole, England).

Systemic administration of HUCB cells 48 hrs post-stroke significantly reduced infarct volume, as evidenced by Fluoro-Jade staining to detect degenerating neurons in coronal brain section taken from rats subjected to MCAO and experimental groups that received HUCB cell treatment. HUCB cell treatment 48 hrs post-stroke significantly reduced infarct volume as time from stroke progressed as compared to MCAO only groups, as seen by samples taken at 72 and 96 hrs post stroke (*$p<0.05$, #$p<0.01$ respectively, as seen in FIGS. 21(A) through (I), and 22. Sham operated groups were not significantly different from HUCB cell treated groups (p>0.05). Furthermore, brain tissues of HUCB cell treatment groups remained intact whereas tissue sections of MCAO only groups were fragile with signs of degradation.

For peroxidase detection, brain tissue sections were washed with PBS for 5 min and incubated in 3% hydrogen peroxide for 20 min. Sections were then washed 3 times in PBS, incubated for 1 hr in permeabilization buffer (2% serum, 0.3% Triton X-100 and 0.3% 1M lysine in PBS) and incubated overnight at 4° C. with primary antibody in antibody solution (2% goat serum, 0.3% Triton X-100 in PBS). The following day, sections were washed with PBS and incubated 1 hr at room temperature with secondary antibody in antibody solution (2% serum, 0.3% Triton X-100 in PBS). Sections were then washed in PBS, incubated in Avidin-Biotin Complex (ABC; Vector Laboratories Inc, Burlingame, Calif.) mixture for 1 hr, washed again and visualized using a DAB/peroxide solution (Vector Laboratories Inc). After 3 final washes, sections were dried, dehydrated with increasing concentrations of EtOH (70%, 95%, 100%), cleared with xylene and coverslipped with DPX. Antibodies consisted of the following: mouse anti-MOG (Abcam, Cambridge, Mass.; 1:250), rabbit anti-Uhmk1 (Protein tech group, Chicago Ill.; 1:50), rabbit anti-Prdx4 (Abcam; 1:250), goat anti-Vcan (Santa Cruz Biotechnology Inc, Santa Cruz, Calif.; 1:50), rabbit anti-Tspn2 (Sigma-Aldrich), goat anti-Insig1 (Santa Cruz Biotechnology Inc; 1:50), and rabbit anti-Mt3 (Sigma-Aldrich; 1:50). Secondary detection was achieved using biotinylated secondary antibodies (Vector Laboratories; 1:300) corresponding to the respective species of primary antibodies.

For fluorescent labeling, tissue sections were subjected to the same method used for peroxidase detection, prior to the secondary antibody incubation, except that fluorescence samples were not incubated in hydrogen peroxide. Double-label immunohistochemistry was achieved by co-incubating the tissues or cells with primary antibodies raised in two distinct species, followed by co-incubation with secondary antibodies conjugated to distinct fluorophores. Following secondary antibody incubation, sections were washed and cover-slipped using VectaShield Hard Set with DAPI (Vector Laboratories). Antibodies used for fluorescent detection consisted of the following: mouse anti-RIP (Millipore, Temecula, Calif.; 1-5000), rabbit anti-Prdx4 (Abcam; 1:500), mouse anti-04 (Chemicon, Temecula, Calif.; 1:1000), mouse anti-OX-42 (AbD Serotec, Kidlington, Oxford, UK; 1:1000), rat anti-MBP (Abcam; 1:1000), rabbit anti-NG2 (Chemicon; 1:500), rabbit anti-Uhmk1 (Protein tech group; 1:50), goat anti-Insig1 (Santa Cruz Biotechnology Inc; 1:50), rabbit anti-Mt3 (Sigma-Aldrich; 1:50), and mouse anti-GFAP (Chemicon; 1:1000). Secondary antibodies used were Alexa Fluor 488 and 594 (Molecular Probe, Eugene, Oreg.; 1:1000). Negative controls were labeled in the absence of primary antibody corresponding with respective secondary, as discussed previously.

For in vivo image analyses, brain sections from >3 animals per group were used. Coronal brain sections encompassing the striatum (Bregma coordinates +1.7 through −0.3) were taken from each animal. Images were generated using a Zeiss Axioskop2 microscope controlled by Openlab (Improvision Ltd, Lexington, Mass.) software. Images were captured with a Zeiss Axiocam Color camera. The ImageJ 1.410 program (National Institutes of Health, USA) was used to measure relative total intensity ratios of ipsilateral vs. contralateral hemispheres. Ratios were calculated for each animal due to ipsilateral brain swelling caused by edema. The group mean total intensity ratio for each experimental treatment group was used for comparisons across treatments. Total intensity analysis was conducted where treatment groups were blinded.

Figure 23:
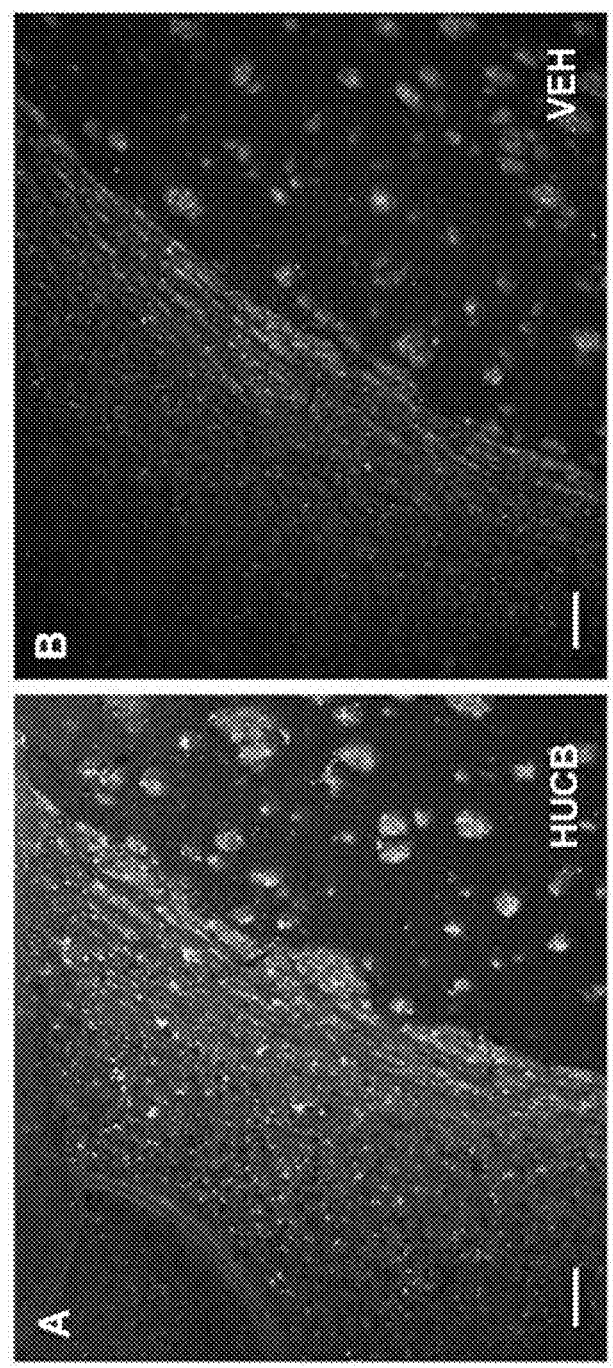
FIGS. 23(A) and (B) are images showing HUCB cells rescue OLs of the external capsule following ischemic insult. O4 immunoreactivity was abundant throughout the ipsilateral external capsule of animals (A) treated with HUCB cells 48 hrs post-MCAO or (B) Vehicle. Vehicle controls also expressed O4, though immunoreactivity was sparsely distributed and less prominent compared to HUCB cell-treated animals. Scales bar=50 μm.
Figure 24:
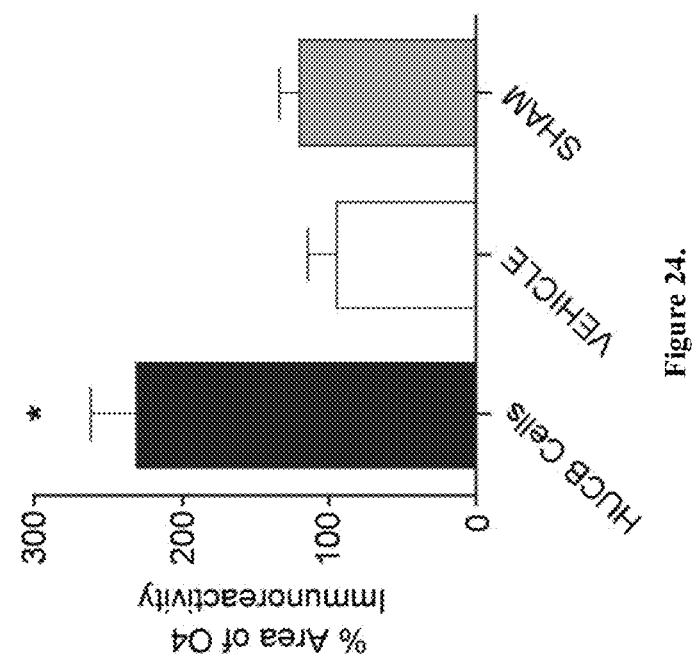
FIG. 24 is a graph showing HUCB cells rescue OLs of the external capsule following ischemic insult. Quantification of results seen in FIG. 21 showed that HUCB cell treatment significantly increased controls (*p<0.05, #p<0.01 n=3).
Figure 25:
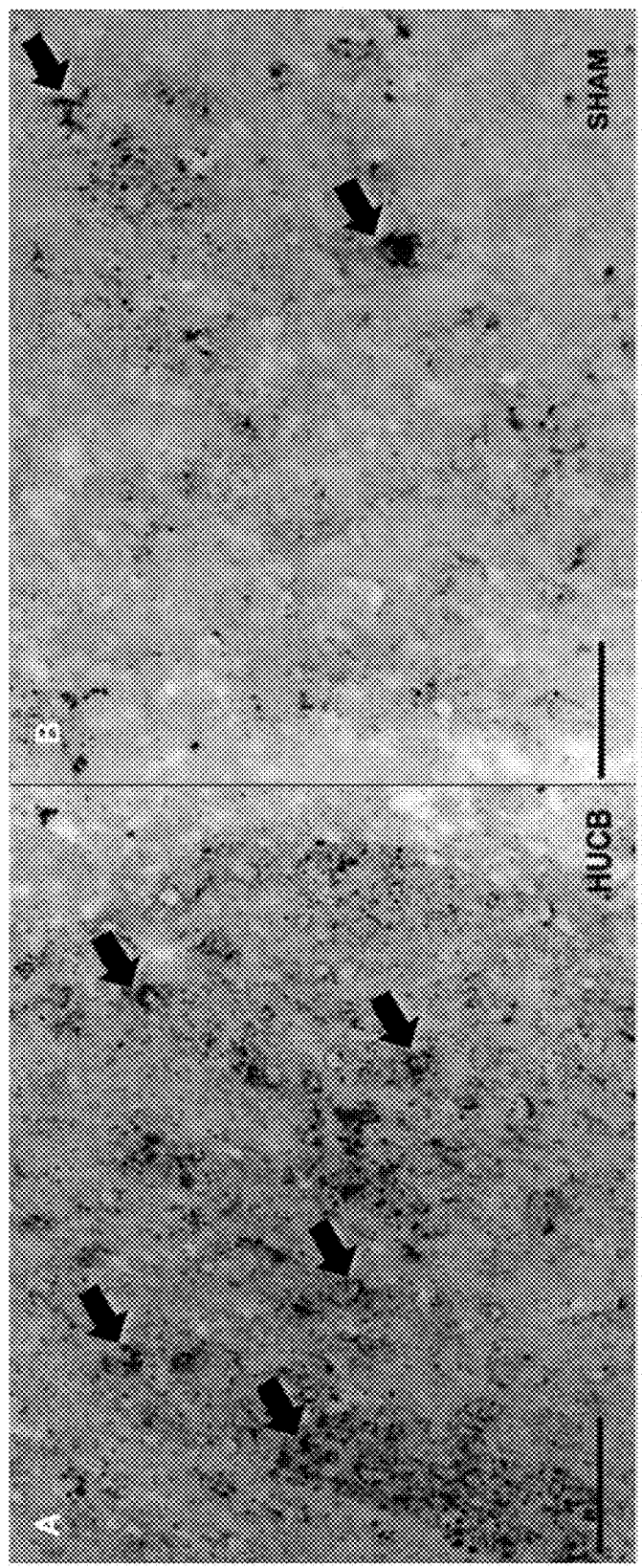
FIGS. 25(A) and (B) are images showing HUCB cells rescue OLs of the external capsule following ischemic insult. O4 immunoreactivity was abundant throughout the ipsilateral external capsule of animals (A) treated with HUCB cells 48 hrs post-MCAO or (B) sham-operated. Sham-operated controls also expressed O4, though immunoreactivity was sparsely distributed and less prominent compared to HUCB cell-treated animals. O4 immunoreactivity relative to both vehicle-treated and sham-operated controls (p<0.01, n=3). Scales bar=50 μm. Arrows points to O4 positive staining.

HUCB cells were administered 48 hrs post-stroke and sections were probed with anti-O4, a highly specific marker of OL cell bodies and processes (Schachner, M., et al., 1981. Developmental expression in central and peripheral nervous system of oligodendrocyte cell surface antigens (0 antigens) recognized by monoclonal antibodies. Dev Biol. 83, 328-38; Sommer, I. and Schachner, M., 1982. Cell that are O4 antigen-positive and O1 antigen-negative differentiate into O1 antigen-positive oligodendrocytes. Neurosci Lett. 29, 183-8), to determine whether this therapy provided oligo-protection. O4 immunoreactivity was ubiquitous throughout the ipsilateral external capsule in sections from animals treated with HUCB cells, as seen in FIG. 23(A), and localized to cell bodies throughout the region, as seen in FIG. 25(A). Sections from vehicle-treated and sham-operated rats also showed O4 immunoreactive cells, though they were sparsely distributed when compared to the ipsilateral hemisphere of HUCB cell treated rats, seen in FIGS. 23(B) and 25(B). Quantification of the percent area occupied by O4 immunoreactivity, seen in FIG. 24, showed that O4 was significantly increased in the ipsilateral hemisphere of animals that received HUCB cells relative to vehicle-treated and sham-operated controls (p<0.01). The administration of HUCBC was found to protect the white matter tract, with protein products localized in the external capsule. It was noted that the external capsule is OL rich.

Figure 26:
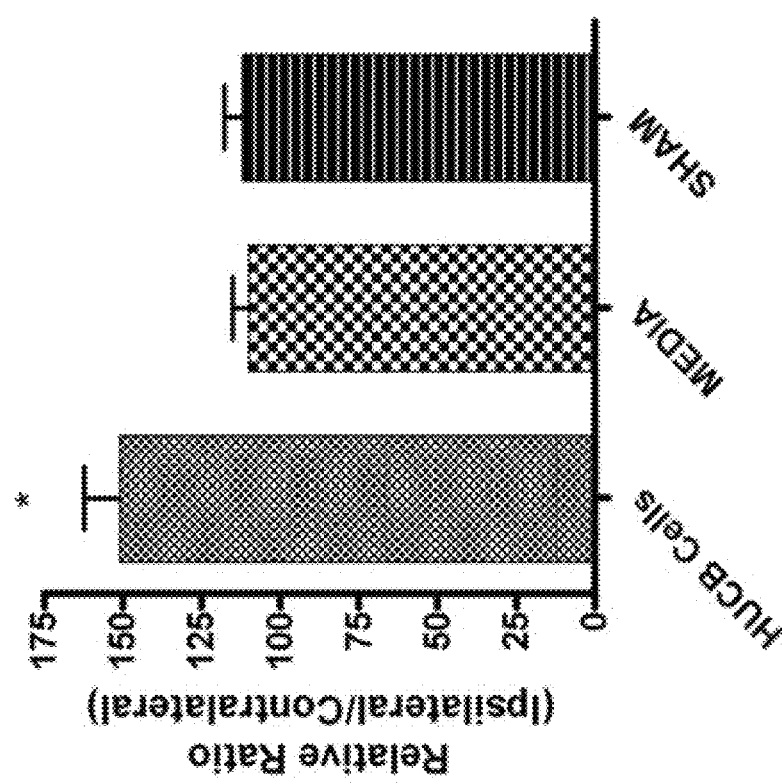
FIG. 26 is a graph showing HUCB cells increased Mt3 expression in the external capsule following MCAO. Mt3 immunostaining was quantified and relative means determined for HUCB cell treatment injections given 48 hrs post-MCAO. An increase in Mt3 expression in the external capsule was seen when compared to media and sham operated controls ($*p<0.01$, n=3).
Figure 27:
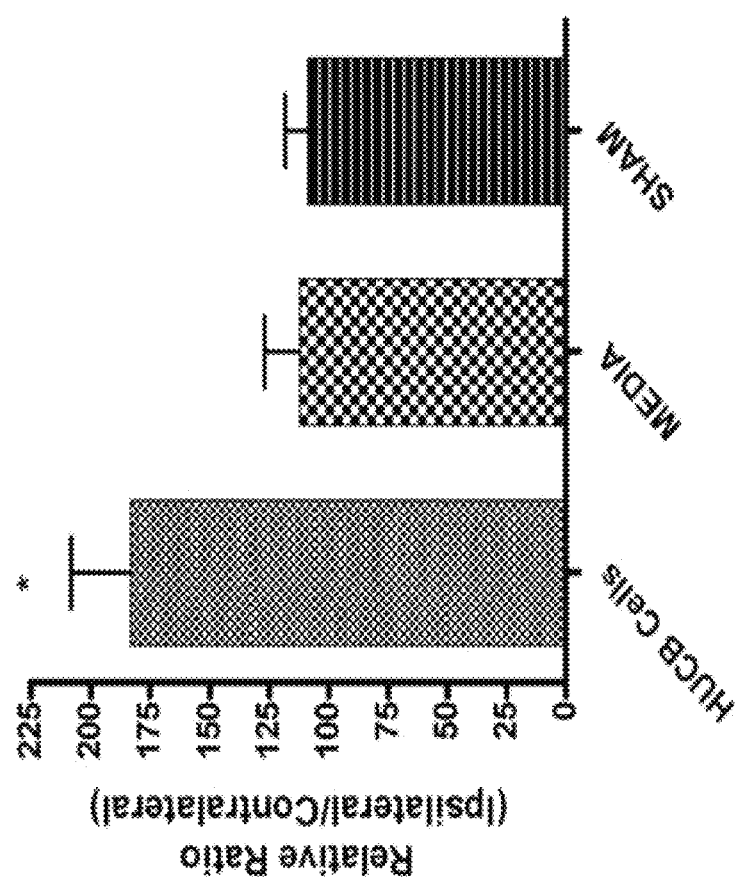
FIG. 27 is a graph showing HUCB cells increased Prdx4 expression in the external capsule following MCAO. Prdx4 immunostaining was quantified and relative means determined for HUCB cell treatment injections given 48 hrs post-MCAO. An increase in Prdx4 expression in the external capsule was seen when compared to media and sham operated controls ($*p<0.05$, n=3).
Figure 28:
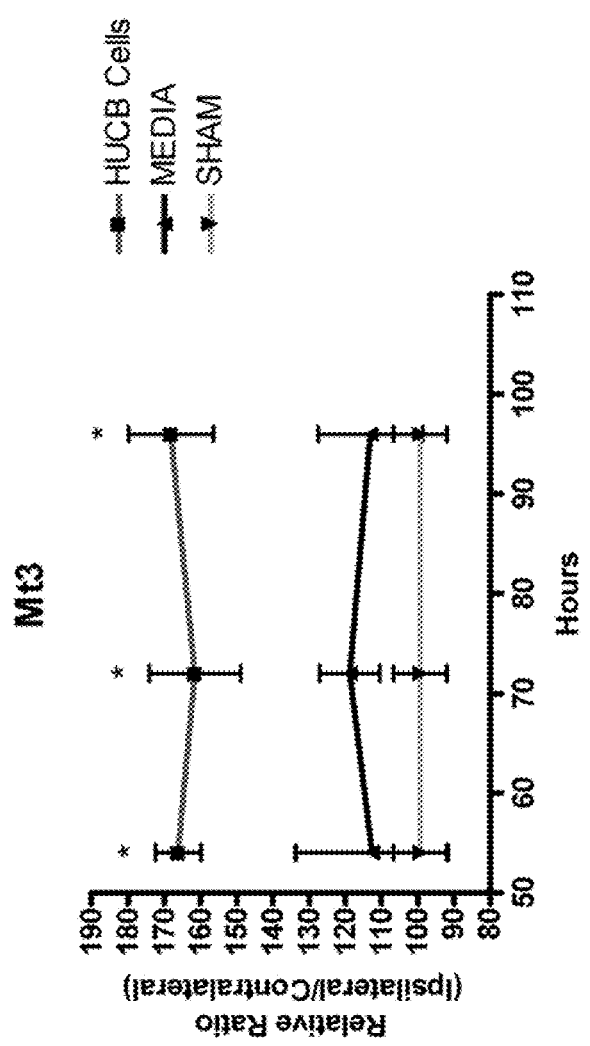
FIG. 28 is a graph showing Mt3 expression time course in the external capsule following MCAO. HUCB cell treatment injections given 48 hrs post-MCAO resulted in increased Mt3 expression when compared to media and sham operated controls in the external capsule at 54, 72 and 96 hrs.
Figure 29:
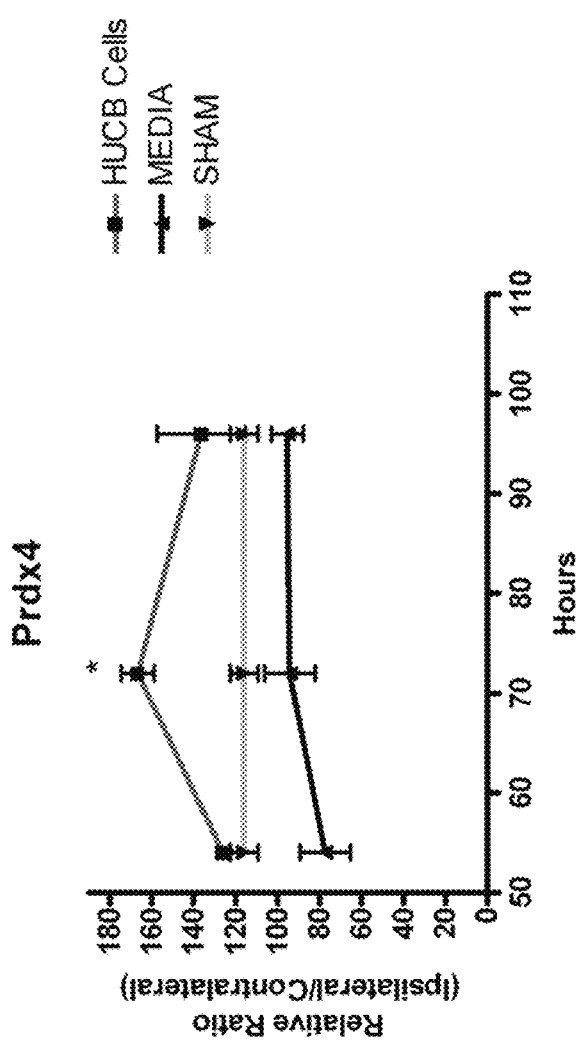
FIG. 29 is a graph showing Prdx4 expression time course in the external capsule following MCAO. HUCB cell treatment injections given 48 hrs post-MCAO resulted in increased Prdx4 expression when compared to media and sham operated controls in the external capsule at 72 hrs.
Figure 30:
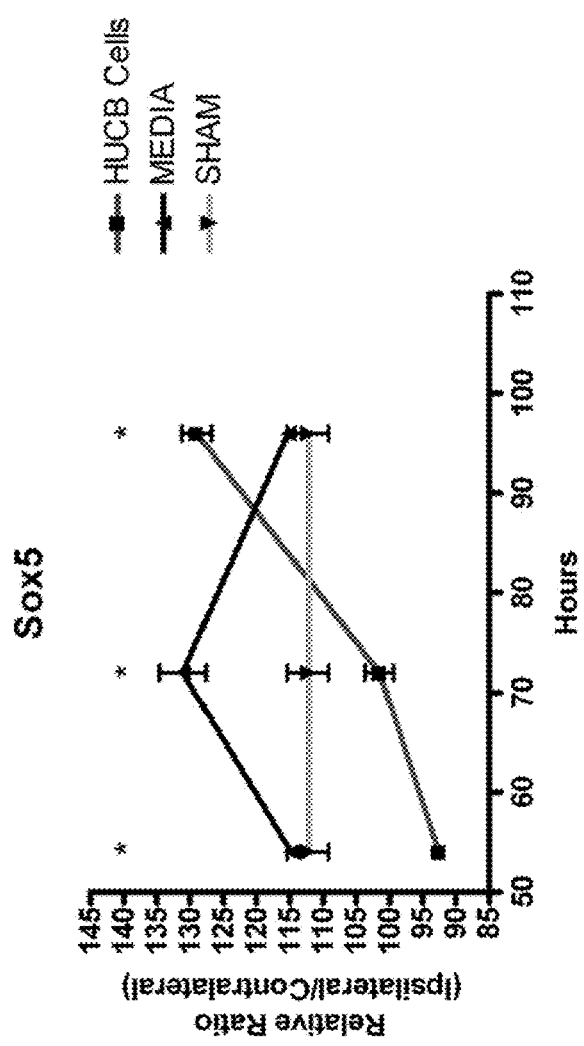
FIG. 30 is a graph showing Sox5 expression time course in the external capsule following MCAO. HUCB cell treatment injections given 48 hrs post-MCAO resulted in decreased Sox5 expression 54 hrs, 72 hrs and increased expression at 96 hrs when compared to media and sham operated controls in the external capsule.

Administration of HUCB cells was also found to increase expression of anti-oxidant protein in the external capsule following MCAO, as seen in FIGS. 26 and 27. Additional testing showed that the anti-oxidant proteins increased following HUCB cell treatment, with peak concentrations obtained by 72 hours in two of three instances, seen in FIGS. 28, 29, 30. Immunohistochemical analysis showed Prdx4 is expressed by astrocytes but not microglia and Mt3 does not co-localize with microglia or astrocytes.

Studies indicate that human umbilical cord blood (HUCB) cells administered systemically at 48 hours post-stroke decrease injury to the brain by 80%. It was found that the HUCB cells release soluble factors that activate intracellular signaling to increase the translation of proteins associated with survival. It was unexpectedly found that leukemia inhibitory factor (LIF) is one of the soluble factors released by HUCB cells.

Figure 31:
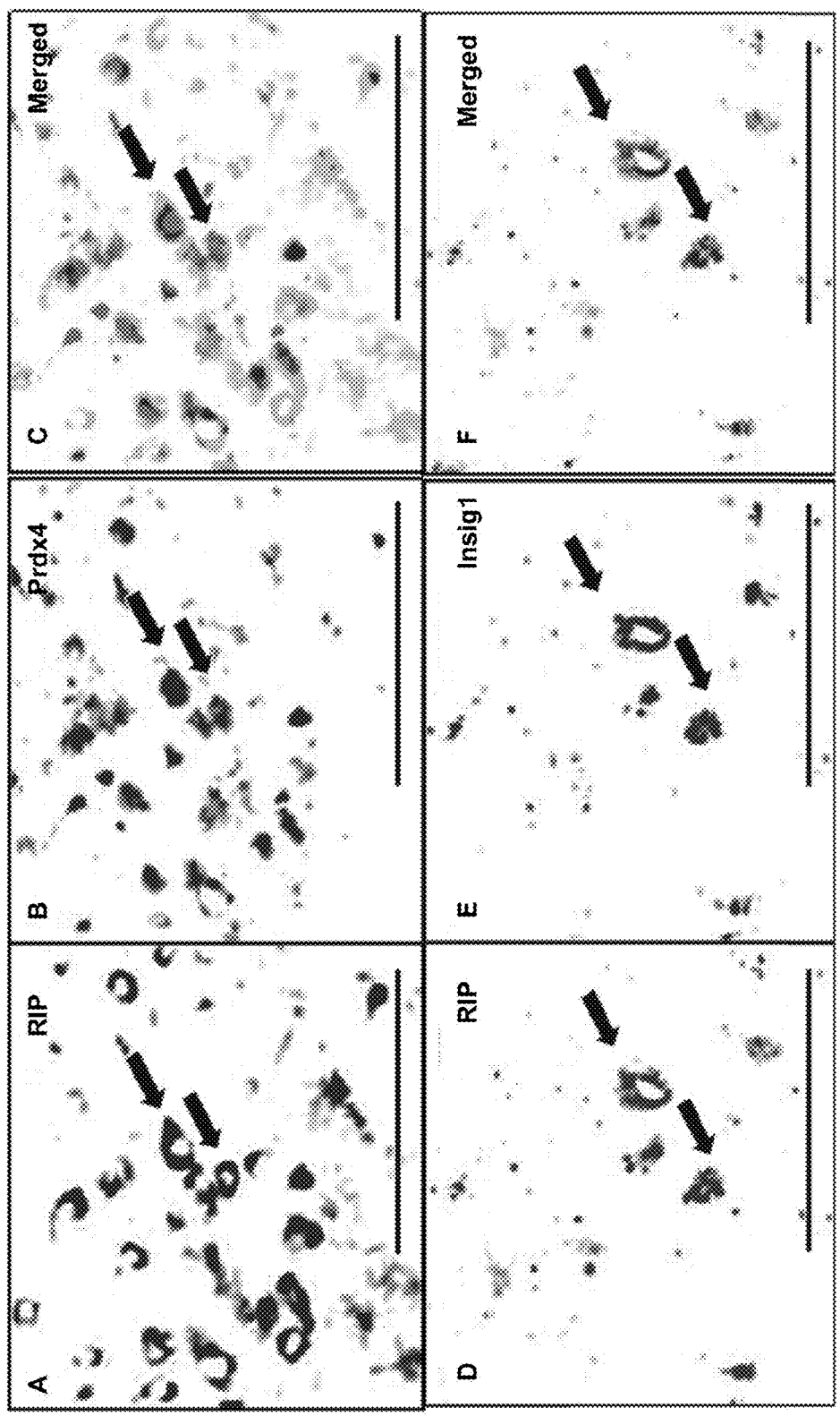
FIGS. 31(A) through (F) are images showing Prdx4 and Insig1 colocalized with OL marker RIP. Photomicrographs depict immunoflourescent double-labeling of OL specific antibody RIP (A, D) and antibodies generated against (B) Prdx4 and Insig1 (E). RIP and Insig1 are colocalized (F) in OL membranes, whereas Prdx4 (C) is cytoplasmically localized. Scale bars=50 μm. Arrows points to positive staining.
Figure 32:
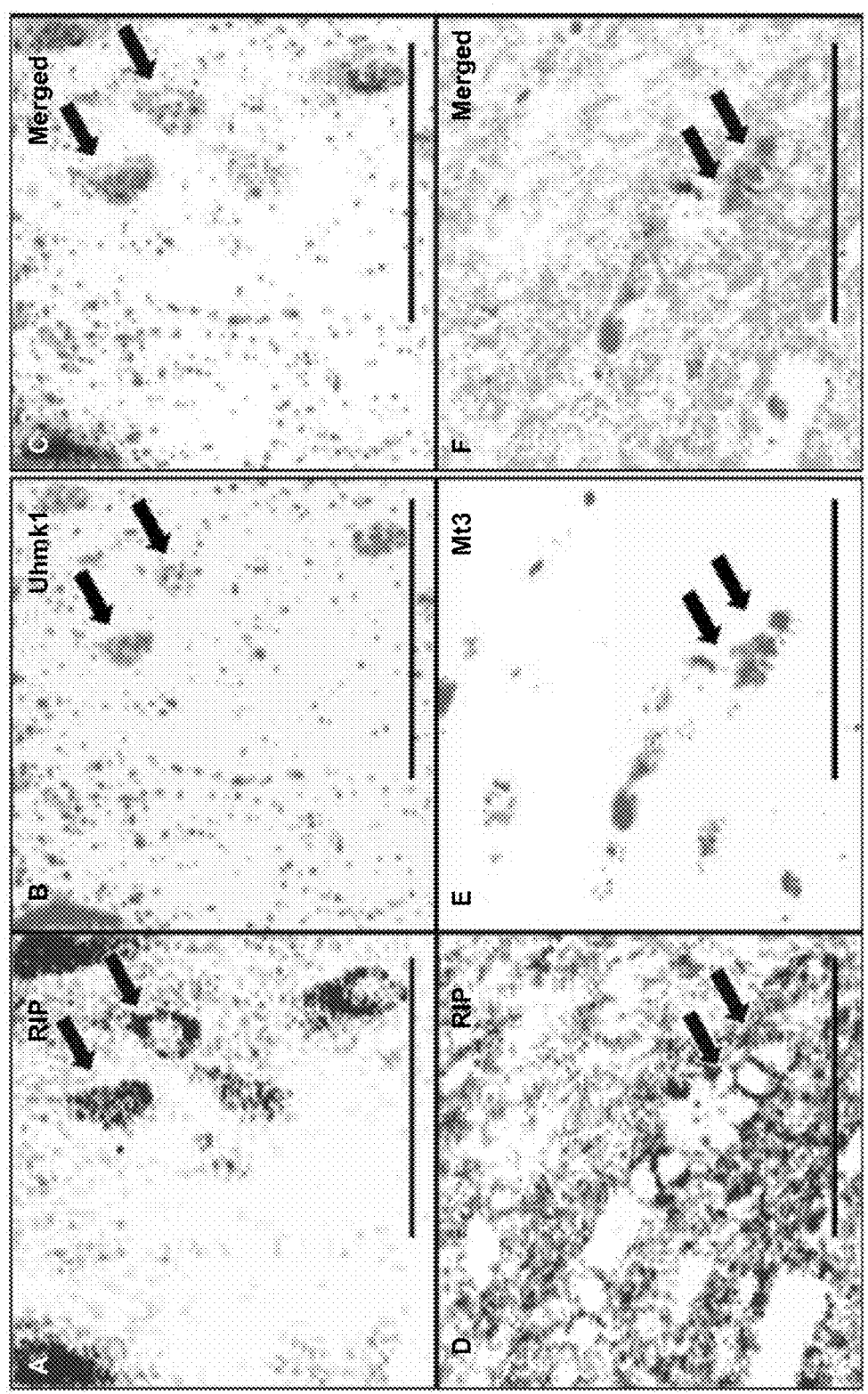
FIGS. 32(A) through (F) are images showing Uhmk1 and Mt3 colocalized with OL marker RIP. Photomicrographs depict immunoflourescent double-labeling of OL specific antibody RIP (A, D) and antibodies generated against (B) Uhmk1 and (E) Mt3. RIP colocalized with Uhmk1 (C) or Mt3 (F) cytoplasmically. Scale bars=50 μm. Arrows points to positive staining.
Figure 33:
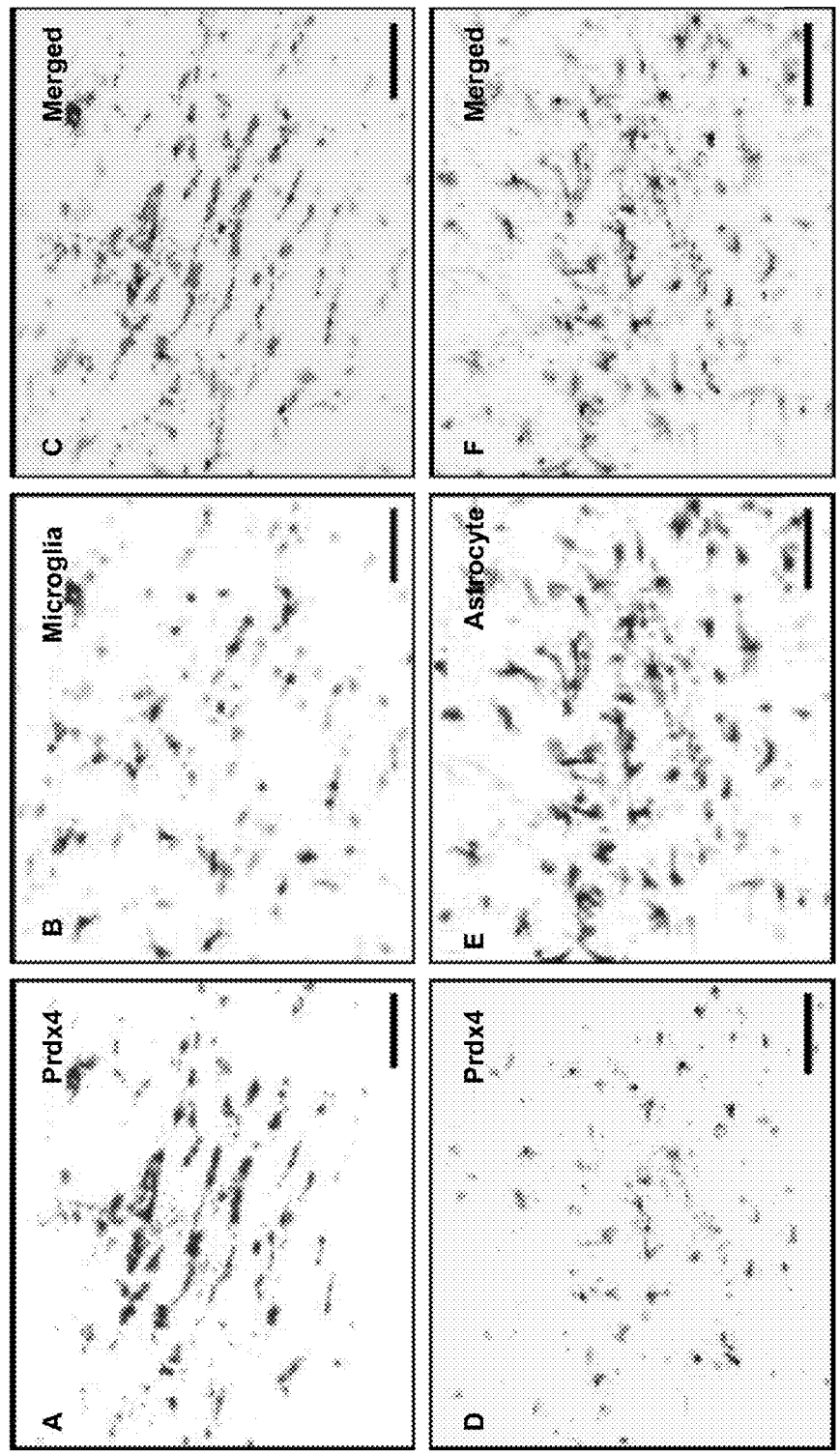
FIGS. 33(A) through (F) are images showing Prdx4 is expressed in astrocytes but not microglia/macrophages following ischemic insult. Double-label immunohistochemistry for Prdx4 (A) and (B) CD11b (microglial stain) shows that Prdx4 is not expressed in CD11b-positive microglia/macrophages (C) contained within the ipsilateral external capsule. (D) Prdx4 and (E) GFAP (astrocytic stain) staining shows colocalization of astrocytic expression with Prdx4 (F) within the white matter following ischemic insult. Scale bars=100 μm.
Figure 34:
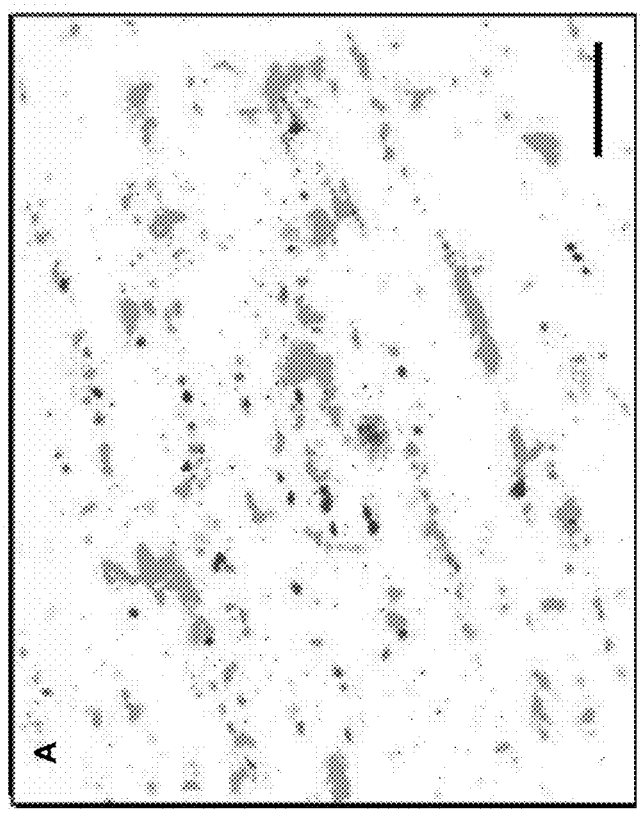
FIGS. 34(A) and (B) show Mt3 is not expressed in microglia/macrophages or astrocytes following ischemic insult. Immunofluorescent double-labeling shows that while expression is evident in the ipsilateral external capsule following MCAO, (A) Mt3 (black) did not colocalize with CD11b (light gray) in microglia/macrophages, or (B) Mt3 (black) did not colocalize with GFAP (light gray) in astrocytes. Scale bars=50 μm.
Figure 34:
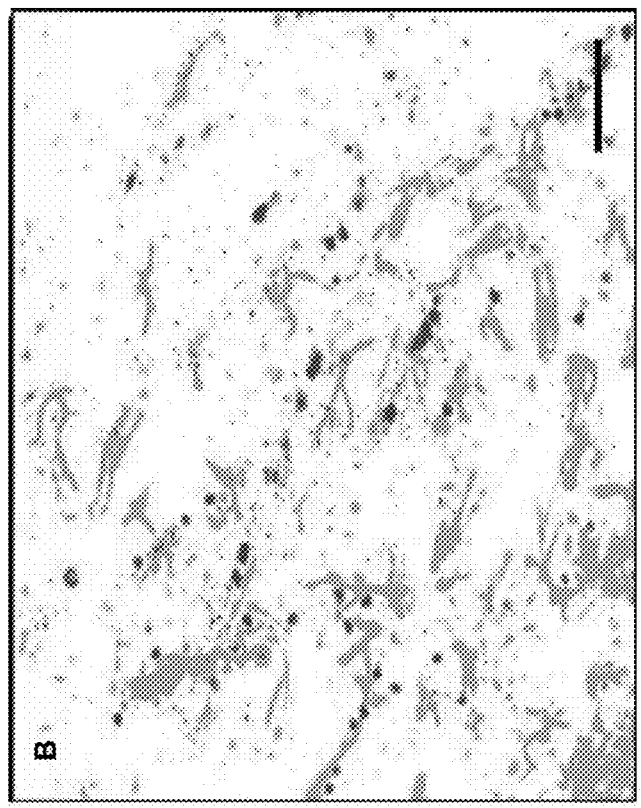
Figure 35:
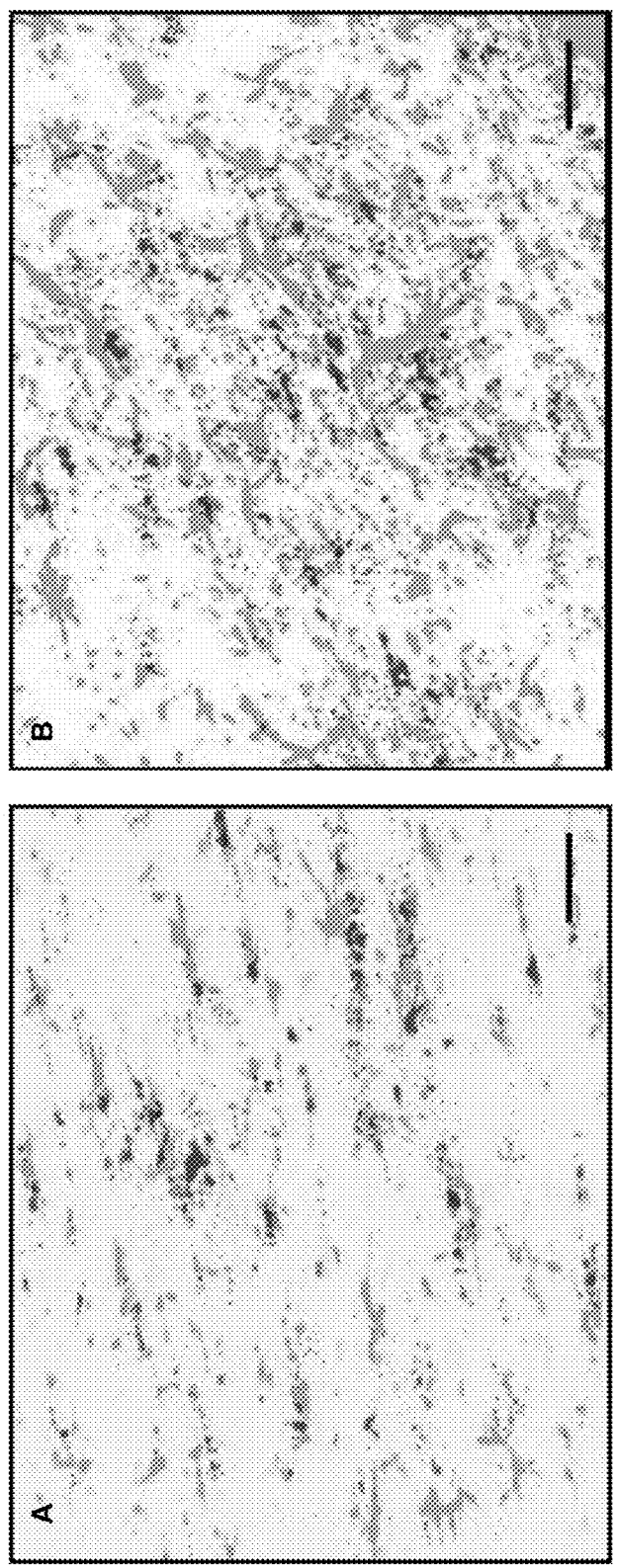
FIGS. 35(A) and (B) show Uhmk1 is not expressed in microglia/macrophages or astrocytes following ischemic insult. Immunofluorescent double-labeling shows that while expression is evident in the ipsilateral external capsule following MCAO, (A) Uhmk1 (black) did not colocalize with CD11b (light gray) in microglia/macrophages, or (B) Uhmk1 (black) did not colocalize with GFAP (light gray) in astrocytes. Scale bars=50 μm.
Figure 36:
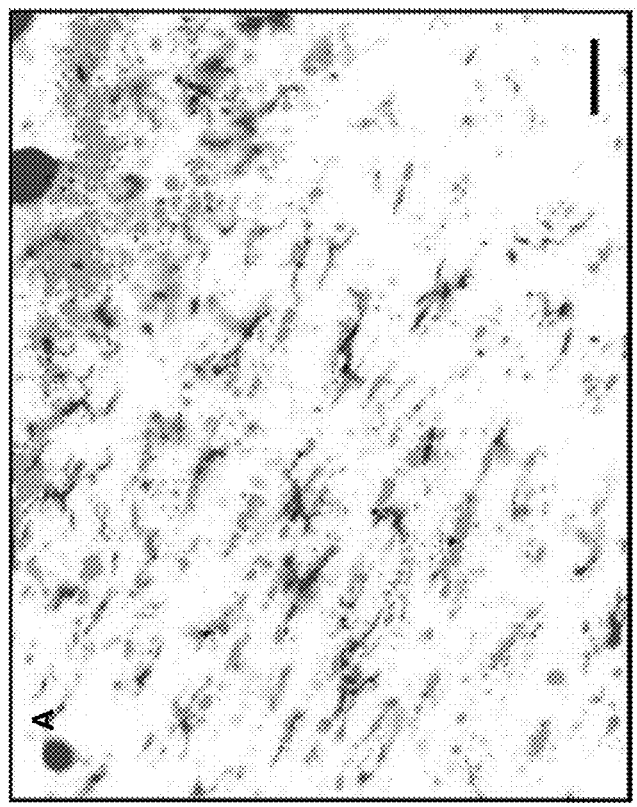
FIGS. 36(A) and (B) show Insig1 is not expressed in microglia/macrophages or astrocytes following ischemic insult. Immunofluorescent double-labeling shows that while expression is evident in the ipsilateral external capsule following MCAO, (A) Insig1 (black) did not colocalize with CD11b (light gray) in microglia/macrophages, or (B) Insig1 (black) did not colocalize with GFAP (light gray) in astrocytes. Scale bars=50 μm.
Figure 36:
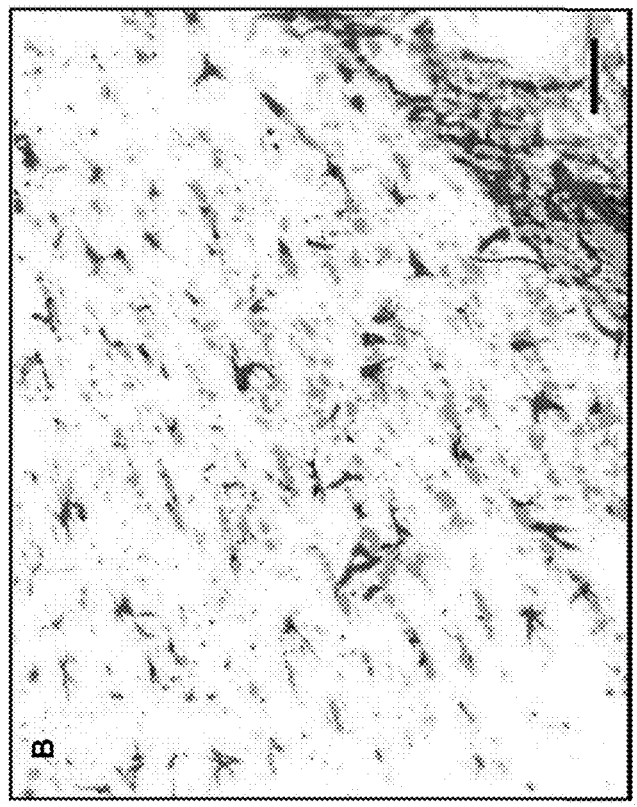

Double-label immunofluorescent staining was performed on sections from animals subjected to MCAO to characterize the cellular expression profile of the identified proteins. RIP, CD11b and GFAP were used for labeling of OL, microglia and astrocytes, respectively, in conjunction with antibodies raised against Prdx4, Mt3, Uhmk1, and Insig1. RIP colocalized with Prdx4, as seen in FIGS. 31(A) through (C), Insig1, seen in FIGS. 31(D) through (F), Uhmk1, as seen in FIGS. 32(A) through (C), and Mt3, as seen in FIGS. 32(D) through (F). RIP staining was localized in OL membranes as does Insig1, whereas, Prdx4 Mt3, and Uhmk1 labeled cytoplasmically. Although Prdx4 did not colocalize with CD11b, as seen in FIGS. 33(A) through (C), Prdx4-positive cell bodies colocalized with GFAP-positive cells that exhibited the classic hypertrophic, stellate morphology indicative of reactive astrocytes, seen in FIGS. 33(D) through (F). Neither CD11b nor GFAP colocalized with Mt3, as seen in FIGS. 34(A) and (B), Uhmk1, seen in FIGS. 35(A) and (B), or Insig1, seen in FIGS. 36(A) and (B).

Example 3

The present study employed both in vitro and in vivo approaches to test the efficacy of HUCB cells in reducing OL cell death and white matter injury, respectively. LDH levels in media from OL cultures co-incubated with HUCB cells during OGD were reduced relative to OL-only cultures. As previously reported (Newcomb, J. D., et al., 2006. Timing of cord blood treatment after experimental stroke determines therapeutic efficacy. Cell Transplant. 15, 213-23; Vendrame, M., et al., 2004. Infusion of human umbilical cord blood cells in a rat model of stroke dose-dependently rescues behavioral deficits and reduces infarct volume. Stroke. 35, 2390-5), HUCB cell treatment 48 hrs post-stroke reduced infarct volume. Separate experiments showed that O4 immunoreactivity increased in the ipsilateral external capsule of rats treated with HUCB cells 48 hrs after MCAO. Upregulation of this OL marker was consistent with the previous report (Hall, A. A., et al., 2009. Human umbilical cord blood cells directly suppress ischemic oligodendrocyte cell death. J Neurosci Res. 87, 333-41) showing that HUCB cell treatment increased MBP immunoreactivity. Thus, HUCB cells not only protect OLs from OGD-induced injury in vitro, but also upregulate the expression of white matter-associated proteins after ischemia in vivo, resulting in protection of the white matter tract.

This work links upregulated expression of genes and gene products with the protective effects of HUCB cell therapy within the context of OL susceptibility and white matter injury resulting from ischemia. HUCB cell-induced upregulation in Prdx4 and Mt3 observed here are consistent with the notion that HUCB cells provide protection to white matter by inducing OLs to express proteins that combat oxidative damage. Oxidative stress is a major cause of OL cell death resulting from OGD (Dewar, D., et al., 2003. Oligodendrocytes and ischemic brain injury. J Cereb Blood Flow Metab. 23, 263-74). The Prdx family of anti-oxidants exerts protective effects through peroxidase activity, detoxifying a range of free radical-forming organic hydroperoxides (Hofmann, B., et al., 2002. Peroxiredoxins. Biol. Chem. 383, 347-64). In particular, Prdx4 regulates the thromboxane A2 receptor, a receptor which is upregulated by oxidative stress and contribute to oxidative injury upon activation (Valentin, F., et al., 2004. The mechanism of oxidative stress stabilization of the thromboxane receptor in COS-7 cells. J Biol. Chem. 279, 8316-24). Previous work showed that thromboxane A2 expression was inhibited during oxidative stress by Prdx4 overexpression (Giguere, P., et al., 2007. Peroxiredoxin-4 interacts with and regulates the thromboxane A(2) receptor. FEBS Lett. 581, 3863-8). In addition, the Prdx family has also been shown to undergo structural changes to engage in chaperone activity in response to excessive oxidation (Jang, H. H., et al., 2004. Two enzymes in one; two yeast peroxiredoxins display oxidative stress-dependent switching from a peroxidase to a molecular chaperone function. Cell. 117, 625-35). This chaperone activity may be a necessary function in the recovery of oxidatively damaged cells by preventing free radical-induced aggregation of cytosolic proteins (Jang, H. H., et al., 2004. Two enzymes in one; two yeast peroxiredoxins display oxidative stressdependent switching from a peroxidase to a molecular chaperone function. Cell. 117, 625-35; Kang, S. W., et al., 2005. 2-Cys peroxiredoxin function in intracellular signal transduction: therapeutic implications. Trends Mol. Med. 11, 571-8).

Similarly, the antioxidant Mt3 exerts its effects through metal detoxification and free radical scavenging activity (Hozumi, I., et al., 1998. Brain injury and growth inhibitory factor (GIF)—a minireview. Neurochem Res. 23, 319-28; Hwang, Y. P., et al., 2008. Metallothionein-III protects against 6-hydroxydopamine-induced oxidative stress by increasing expression of heme oxygenase-1 in a PI3K and ERK/Nrf2-dependent manner. Toxicol Appl Pharmacol. 231, 318-27; Uchida, Y., et al., 2002. Growth inhibitory factor prevents neurite extension and the death of cortical neurons caused by high oxygen exposure through hydroxyl radical scavenging. J Biol. Chem. 277, 32353-9). These mechanisms are of particular relevance since iron is not only a critical co-factor in myelin production, but is also highly reactive and can contribute to free radical formation and lipid peroxidation (Braughler, J. M., et al., 1986. The involvement of iron in lipid peroxidation. Importance of ferric to ferrous ratios in initiation. J Biol. Chem. 261, 10282-9; Connor, J. R. and Menzies, S. L., 1996. Relationship of iron to oligodendrocytes and myelination. Glia. 17, 83-93). Additionally, OLs possess low concentrations of the antioxidant glutathione, and oxidative stress leads to increased iron-mediated production of ROS (Juurlink, B. H., 1997. Response of glial cells to ischemia: roles of reactive oxygen species and glutathione. Neurosci Biobehav Rev. 21, 151-66; Juurlink, et al., 1998. Peroxide-scavenging deficit underlies oligodendrocyte susceptibility to oxidative stress. Glia. 22, 371-8). Thus, the protective effects of HUCB cells result, at least in part, from the secretion of at least leukemia inhibitory factor and granulocyte colony stimulating factor that ultimately increase the expression of Mt3.

HUCB cell therapy has previously been shown to target the Akt signaling pathway, as Akt inhibition diminishes the protective effects of HUCB cells (Dasari, V. R., et al., 2008. Neuroprotection by cord blood stem cells against glutamate-induced apoptosis is mediated by Akt pathway. Neurobiol Dis. 32, 486-98). Importantly, growth factors such as VEGF and interleukins such as IL-6, which are secreted by HUCB cells, have also been shown to activate Akt, leading to cell migration, angiogenesis, and cell survival (Morales-Ruiz, M., et al., 2000. Vascular endothelial growth factor-stimulated actin reorganization and migration of endothelial cells is regulated via the serine/threonine kinase Akt. Circ Res. 86, 892-6; Neuhoff, S., et al., 2007. Proliferation, differentiation, and cytokine secretion of human umbilical cord blood-derived mononuclear cells in vitro. Exp Hematol. 35, 1119-31; Six, I., et al., 2002. Akt signaling mediates VEGF/VPF vascular permeability in vivo. FEBS Lett. 532, 67-9; Wegiel, B., et al., 2008. Interleukin-6 activates PI3K/Akt pathway and regulates cyclin A1 to promote prostate cancer cell survival. Int J. Cancer. 122, 1521-9). The present study identified several common transcription factor binding sites within the promoter regions of the genes identified by microarray. In particular, EVI1, MZF1, and GATA1 transcription occur downstream of PI3k/Akt activation (Liu, Y., et al., 2006. Evi1 is a survival factor which conveys resistance to both TGFbeta- and taxol-mediated cell death via PI3K/AKT. Oncogene. 25, 3565-75; Moeenrezakhanlou, A., et al., 2008. Myeloid cell differentiation in response to calcitriol for expression CD11b and CD14 is regulated by myeloid zinc finger-1 protein downstream of phosphatidylinositol 3-kinase. J Leukoc Biol. 84, 519-28; Yu, Y. L., et al., 2005. MAPK-mediated phosphorylation of GATA-1 promotes Bcl-XL expression and cell survival. J Biol. Chem. 280, 29533-42), providing additional evidence that Akt is an important upstream activator responsible for the oligoprotective, anti-oxidant effects of HUCB cells. Taken together, these data show that HUCB cells release factors that transduce signaling converging on Akt, thereby increasing the transcription of oligoprotective genes.

In addition to combating oxidative stress, data here show that HUCB cell treatment alters the expression of proteins involved in microtubule regulation. The concerted actions of MOG and Stmn2 inhibit microtubule polymerization, and Stmn2 was previously found to increase neurite outgrowth via this mechanism (Chiellini, C., et al., 2008. Stathmin-like 2, a developmentallyassociated neuronal marker, is expressed and modulated during osteogenesis of human mesenchymal stem cells. Biochem Biophys Res Commun. 374, 64-8; Johns, T. G. and Bernard, C. C., 1999. The structure and function of myelin oligodendrocyte glycoprotein. J. Neurochem. 72, 1-9; Riederer, B. M., et al., 1997. Regulation of microtubule dynamics by the neuronal growth-associated protein SCG10. Proc Natl Acad Sci USA. 94, 741-5). Thus, these data provide evidence that upregulated expression of MOG and/or Stmn2 acts to inhibit microtubule polymerization in OLs, thereby increasing proliferation and/or migration and enhancing white matter repair.

Indeed, previous findings showed that mature OLs retain the ability to proliferate following injury (Wood, P. M. and Bunge, R. P., 1991. The origin of remyelinating cells in the adult central nervous system: the role of the mature oligodendrocyte. Glia. 4, 225-32). In addition to regulating microtubule dynamics through the phosphorylation of Stmn2 (Belmont, L. D. and Mitchison, T. J., 1996. Identification of a protein that interacts with tubulin dimers and increases the catastrophe rate of microtubules. Cell. 84, 623-31), Uhmk1 induces proliferation and cell cycle progression through the phosphorylation of p27kip1 (Nakamura, S., et al., 2008. KIS induces proliferation and the cell cycle progression through the phosphorylation of p27Kip1 in leukemia cells. Leuk Res. 32, 1358-65). Interestingly, Uhmk1 was also upregulated after MCAO in HUCB cell-treated rats. Here, the observed elevations in both Uhmk1 and O4 expression support the notion that HUCB cell therapy protects white matter injury by inducing OL proliferation via this pathway.

HUCB cell therapy may also alleviate white matter injury through replacement of important somatic and/or axonal membrane lipids that are degraded in response to H-I injury. The OL axon sheath is rich in glycosphingolipids and cholesterol (Simons, M. and Trajkovic, K., 2006. Neuron-glia communication in the control of oligodendrocyte function and myelin biogenesis. J Cell Sci. 119, 4381-9). Insig1 is degraded when cholesterol is depleted within a cell (Gong, Y., et al., 2006. Sterolregulated ubiquitination and degradation of Insig-1 creates a convergent mechanism for feedback control of cholesterol synthesis and uptake. Cell Metab. 3, 15-24), and hypoxia increases Insig1 expression through a mechanism mediated by hypoxia inducible factor 1α (Nguyen, A. D., et al., 2007. Hypoxia stimulates degradation of 3-hydroxy-3-methylglutaryl-coenzyme A reductase through accumulation of lanosterol and hypoxia-inducible factor-mediated induction of insigs. J Biol. Chem. 282, 27436-46). Thus, the elevations in Insig1 likely reflect HUCB cell induction of cholesterol biosynthesis aimed at remyelination or restoration of the cell membrane.

Tspan2 is integrated into the myelin sheath membrane following active myelination, while Vcan is involved in OL migration, proliferation, and structural integrity (Birling, M. C., et al., 1999. A novel rat tetraspan protein in cells of the oligodendrocyte lineage. J. Neurochem. 73, 2600-8; Sheng, W., et al., 2005. The roles of versican V1 and V2 isoforms in cell proliferation and apoptosis. Mol Biol Cell. 16, 1330-40). Tspan2 and Vcan mRNAs were upregulated in OL cultures subjected to OGD and treated with HUCB cells, yet there was no significant difference in protein expression in vivo after MCAO. These data suggest that although Vcan and Tspan may be capable of enhancing axonal and/or plasma membrane viability in culture, the complex microenvironment present in the stroked brain determines which genes are translated and trafficked accordingly. Likewise, these differences in in vitro transcription and in vivo translation highlight the importance of combining multiple approaches to elucidate the protective pathways elicited by HUCB cells.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a method of upregulating anti-oxidant proteins in neurons to effect treatment and prevent neuronal damage, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of treating stroke-induced oligodendrocytes death, comprising:
    administering isolated leukemia inhibitory factor systemically into a circulatory vessel to a patient experiencing stroke-induced oligodendrocyte death,
    wherein the leukemia inhibitory factor is administered from 24 hours to 48 hours of the stroke.

2. The method of claim 1, wherein the leukemia inhibitory factor is administered at 48 hours of the stroke.

3. The method of claim 1, wherein the leukemia inhibitory factor is produced by human umbilical cord blood cells.

4. The method of claim 1, wherein the leukemia inhibitory factor is administered intravenously.

5. A method of enhancing replacement of membrane lipids that are degraded in response to stroke, comprising:
    administering isolated leukemia inhibitory factor systemically into a circulatory vessel to a patient in need thereof,
    wherein the leukemia inhibitory factor is administered from 24 hours to 48 hours of the stroke.

6. The method of claim 5, wherein the leukemia inhibitory factor is administered at 48 hours of the stroke.

7. The method of claim 5, wherein the leukemia inhibitory factor is isolated from secretion of human umbilical cord blood cells.

8. The method of claim 5, wherein the leukemia inhibitory factor is administered intravenously.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: artificial
<220> FEATURE:
<223> OTHER INFORMATION: RT-PCR reverse primer

<400> SEQUENCE: 1
ttttaggcat tgcccatctc                                          20

<210> SEQ ID NO 2
<211> LENGTH: 20
<212> TYPE: DNA
<213> ORGANISM: artificial
```

```
<220> FEATURE:
<223> OTHER INFORMATION: RT-PCR forward primer

<400> SEQUENCE: 2
atgacgtccc ctgcaactac                                                    20
```